(12) United States Patent
Buxton et al.

(10) Patent No.: US 8,637,512 B2
(45) Date of Patent: Jan. 28, 2014

(54) FORMULATIONS AND METHOD OF TREATMENT

(75) Inventors: Ian Richard Buxton, Mississauga (CA); Wlodzimierz Karolak, Mississauga (CA); Mehran Maleki, Mississauga (CA); Vijay Mohan Iyer, Mississauga (CA)

(73) Assignee: Glaxo Group Limited, Brentford, Middlesex (GB)

( * ) Notice: Subject to any disclaimer, the term of this patent is extended or adjusted under 35 U.S.C. 154(b) by 1782 days.

(21) Appl. No.: 10/726,752

(22) Filed: Dec. 2, 2003

(65) Prior Publication Data

US 2004/0192690 A1  Sep. 30, 2004

Related U.S. Application Data

(63) Continuation-in-part of application No. 10/629,177, filed on Jul. 29, 2003, now abandoned.

(30) Foreign Application Priority Data

Jul. 29, 2002 (GB) .................................. 0217492.8
Jul. 29, 2002 (GB) .................................. 0217493.6
Jun. 13, 2003 (GB) .................................. 0313801.3

(51) Int. Cl.
    *A61K 31/53* (2006.01)
    *A61K 9/22* (2006.01)
    *A61P 25/08* (2006.01)

(52) U.S. Cl.
    USPC ........................... 514/242; 424/468; 424/497

(58) Field of Classification Search
    USPC ........................... 514/241, 242; 424/468, 497
    See application file for complete search history.

(56) References Cited

U.S. PATENT DOCUMENTS

| | | | |
|---|---|---|---|
| 4,449,983 A | 5/1984 | Cortese et al. | |
| 4,556,552 A | 12/1985 | Porter et al. | |
| 4,602,017 A | 7/1986 | Sawyer et al. | |
| 4,704,295 A | 11/1987 | Porter et al. | |
| 4,769,027 A | 9/1988 | Baker et al. | |
| 4,775,536 A | 10/1988 | Patell | |
| 4,816,262 A | 3/1989 | McMullen | |
| 4,983,401 A | 1/1991 | Eichel et al. | |
| 5,004,614 A * | 4/1991 | Staniforth ..................... 424/466 | |
| 5,242,627 A | 9/1993 | Lundin | |
| 5,326,571 A | 7/1994 | Wright et al. | |
| 5,342,627 A | 8/1994 | Chopra et al. | |
| 5,366,738 A | 11/1994 | Rork et al. | |
| 5,431,921 A | 7/1995 | Thombre | |
| 5,500,227 A | 3/1996 | Oshlack et al. | |
| 5,520,931 A | 5/1996 | Persson et al. | |
| 5,863,558 A | 1/1999 | Jao et al. | |
| 5,876,750 A | 3/1999 | Jao et al. | |
| 5,906,832 A | 5/1999 | Jao et al. | |
| 5,955,103 A * | 9/1999 | Jao et al. ........................ 424/457 |
| 6,039,976 A | 3/2000 | Mehra et al. | |
| 6,264,985 B1 | 7/2001 | Cremer | |
| 6,287,599 B1 | 9/2001 | Burnside et al. | |
| 6,387,403 B1 | 5/2002 | Seroff et al. | |
| 6,387,404 B2 | 5/2002 | Oshlack et al. | |
| 6,406,716 B2 | 6/2002 | Caruso et al. | |
| 6,475,521 B1 | 11/2002 | Timmins et al. | |
| 6,569,463 B2 | 5/2003 | Patel et al. | |
| 6,607,751 B1 | 8/2003 | Odidi et al. | |
| 6,667,060 B1 | 12/2003 | Vandecruys et al. | |
| 6,787,156 B1 | 9/2004 | Bar-Shalom | |
| 2002/0012675 A1 * | 1/2002 | Jain et al. ..................... 424/400 |
| 2002/0051814 A1 | 5/2002 | Chen | |
| 2002/0127263 A1 | 9/2002 | Carlyle et al. | |
| 2002/0136744 A1 | 9/2002 | McGlynn et al. | |
| 2003/0056896 A1 | 3/2003 | Jao et al. | |
| 2003/0203027 A1 | 10/2003 | Verreck et al. | |
| 2004/0018327 A1 | 1/2004 | Wynn et al. | |
| 2004/0062806 A1 | 4/2004 | Martini et al. | |
| 2004/0146556 A1 | 7/2004 | Noack et al. | |
| 2004/0192690 A1 | 9/2004 | Buxton et al. | |
| 2004/0219209 A1 | 11/2004 | Chen et al. | |
| 2004/0245675 A1 | 12/2004 | Clarke et al. | |
| 2005/0163845 A1 | 7/2005 | Conte et al. | |
| 2005/0175700 A1 | 8/2005 | Li et al. | |
| 2007/0134326 A1 | 6/2007 | Hoke et al. | |
| 2007/0141146 A1 | 6/2007 | Re et al. | |
| 2007/0275054 A1 | 11/2007 | Lewis et al. | |
| 2007/0275063 A1 | 11/2007 | Benincosa et al. | |
| 2007/0281023 A1 | 12/2007 | Glinecke et al. | |
| 2008/0014266 A1 | 1/2008 | Lewis et al. | |
| 2008/0124393 A1 * | 5/2008 | Swanson et al. .............. 424/465 |
| 2008/0130624 A1 | 6/2008 | Re | |
| 2008/0166408 A1 | 7/2008 | Heafield et al. | |
| 2008/0206336 A1 | 8/2008 | Coles et al. | |
| 2011/0135695 A1 | 6/2011 | Li et al. | |

FOREIGN PATENT DOCUMENTS

| | | |
|---|---|---|
| EP | 0 021 121 | 5/1980 |
| EP | 0 166 319 | 3/1993 |
| EP | 0 631 775 | 8/1999 |
| GB | 2150830 | 7/1985 |

(Continued)

OTHER PUBLICATIONS

Rohm Pharma polymers (2001, p. 1-4).*
Leandri et al., "*Lamotrigine in trigeminal neuralgia secondary to multiple sclerosis*",J. Neurol,vol. 247,pp. 556-558, (Jan. 25, 2000).
Datasheet for Registration of EUDRAGIT® Acrylic Polymers. International Availability and Acceptance for Use in the Manufacture of Pharmaceutical Dosage Forms. 1999.
Practical Course in Film Coating of Pharmaceutical Dosage Forms with EUDRAGIT®, http://www.roehm.de/en/pharmapolymers?content=/en/pharmacopolymers/service/literature/practical_course Mar. 2000.

(Continued)

*Primary Examiner* — Sreeni Padmanabhan
*Assistant Examiner* — Irina Neagu
(74) *Attorney, Agent, or Firm* — Robert H. Brink

(57) ABSTRACT

A sustained release formulation of lamotrigine or a pharmaceutically acceptable derivative thereof and methods of treatment and uses thereof.

3 Claims, 12 Drawing Sheets

(56) References Cited

FOREIGN PATENT DOCUMENTS

Figure 4A:
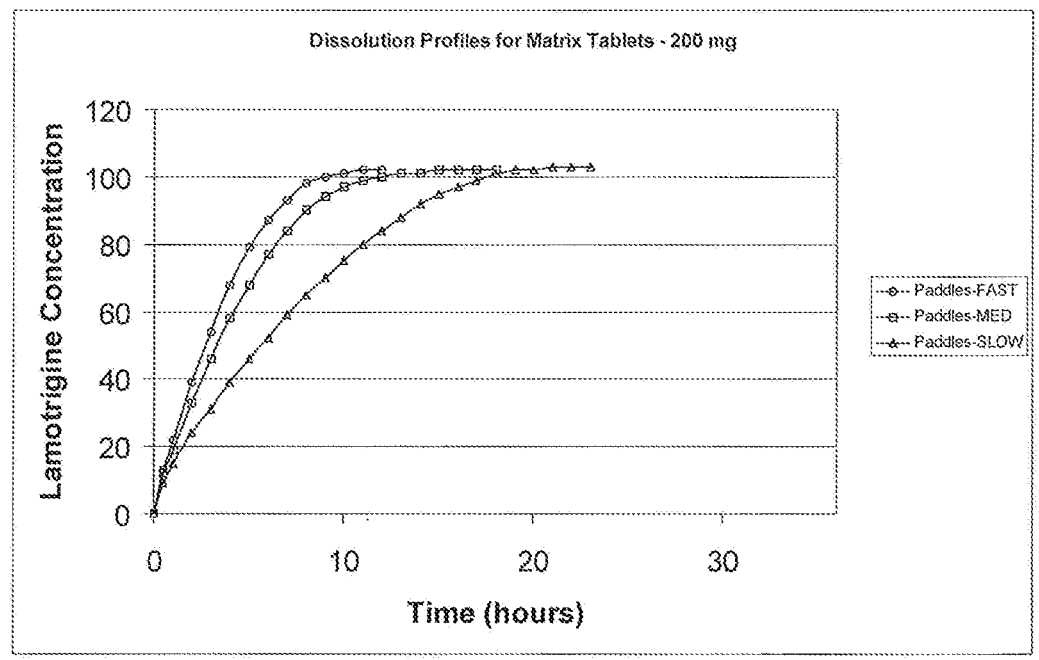

| | | |
|---|---|---|
| WO | 90/01925 | 3/1990 |
| WO | 92/13527 | 8/1992 |
| WO | 93/09785 | 5/1993 |
| WO | 95/22962 | 8/1995 |
| WO | 95/28927 | 11/1995 |
| WO | 95/29665 | 11/1995 |
| WO | 96/01612 | 1/1996 |
| WO | 96/17611 | 6/1996 |
| WO | 97/14415 | 4/1997 |
| WO | 98/47491 | 10/1998 |
| WO | 99/11211 | 3/1999 |
| WO | 99/26606 | 6/1999 |
| WO | 99/48481 | 9/1999 |
| WO | 99/51208 | 10/1999 |
| WO | 0059477 A1 | 10/2000 |
| WO | 01/37808 | 5/2001 |
| WO | 01/47498 | 7/2001 |
| WO | 02/17918 | 3/2002 |
| WO | 02/34240 | 5/2002 |
| WO | 02/38131 | 5/2002 |
| WO | 02/055009 | 7/2002 |
| WO | 03/024430 | 3/2003 |
| WO | 03/026625 | 4/2003 |
| WO | 03/026626 | 4/2003 |
| WO | 03/053400 | 7/2003 |
| WO | 03/063823 | 8/2003 |
| WO | 03/063868 | 8/2003 |
| WO | 03/068195 | 8/2003 |
| WO | 03/070225 | 8/2003 |
| WO | 03/075893 | 9/2003 |
| WO | 03/075894 | 9/2003 |
| WO | 03/075897 | 9/2003 |
| WO | 03/082207 | 10/2003 |
| WO | 03/086364 | 10/2003 |
| WO | 03/090732 | 11/2003 |
| WO | 03/092649 | 11/2003 |
| WO | 03/092660 | 11/2003 |
| WO | 03/094888 | 11/2003 |
| WO | 03/096968 | 11/2003 |
| WO | 03/101384 | 12/2003 |
| WO | 03/103637 | 12/2003 |
| WO | WO 03/104192 | * 12/2003 |
| WO | 2005/013935 | 2/2005 |
| WO | 2005/013956 | 2/2005 |

OTHER PUBLICATIONS

ACRYL-EZE®, Product Information (2008), www.colorcon.com/products/coatings/enteric-delayed-release/acryl-eze.

* cited by examiner

Figure 1: Simulated lamotrigine pharmacokinetic profile for 200mg lamotrigine (Lamictal™) dose administered twice daily.
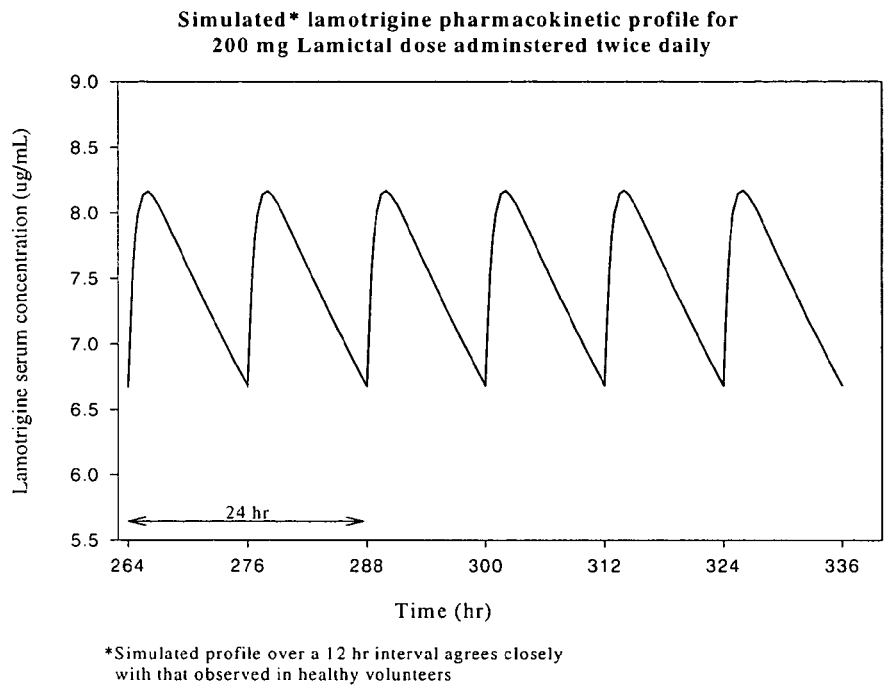
Figure 2: Dissolution profile of three different batches of lamotrigine (Lamictal™) 150mg tablets.
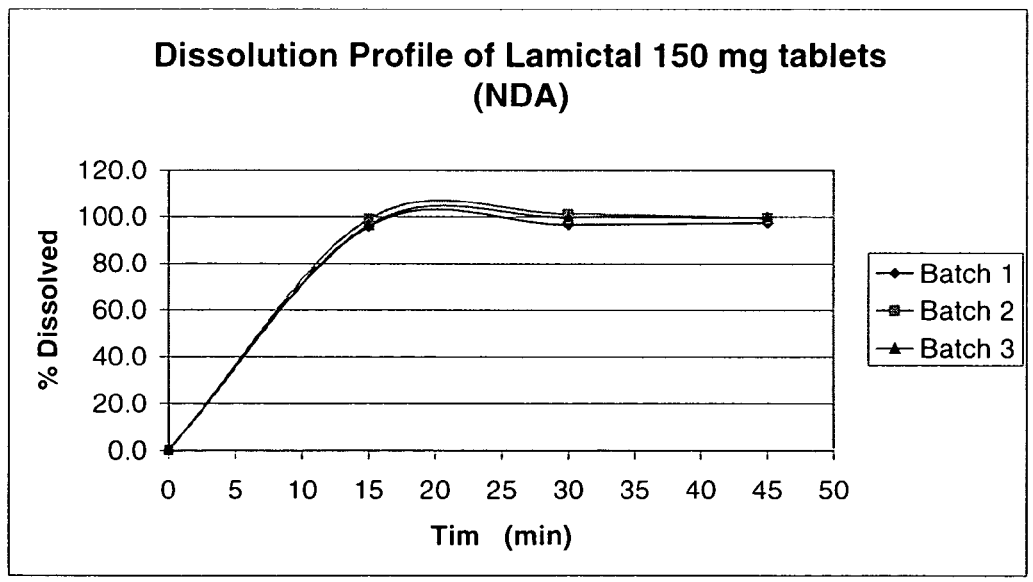

Figure 3a: Matrix Tablet From Example 1 with 35% Polymer
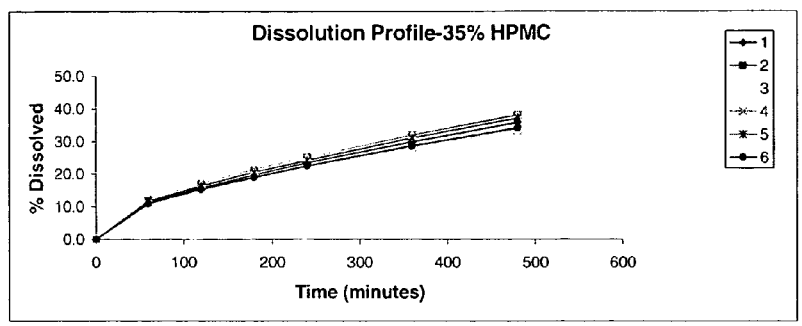
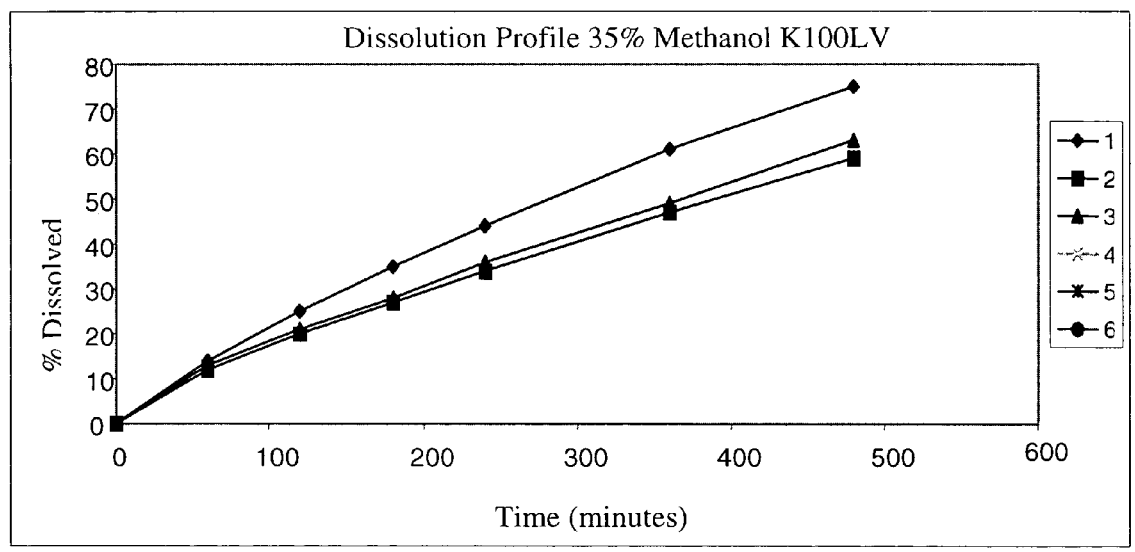
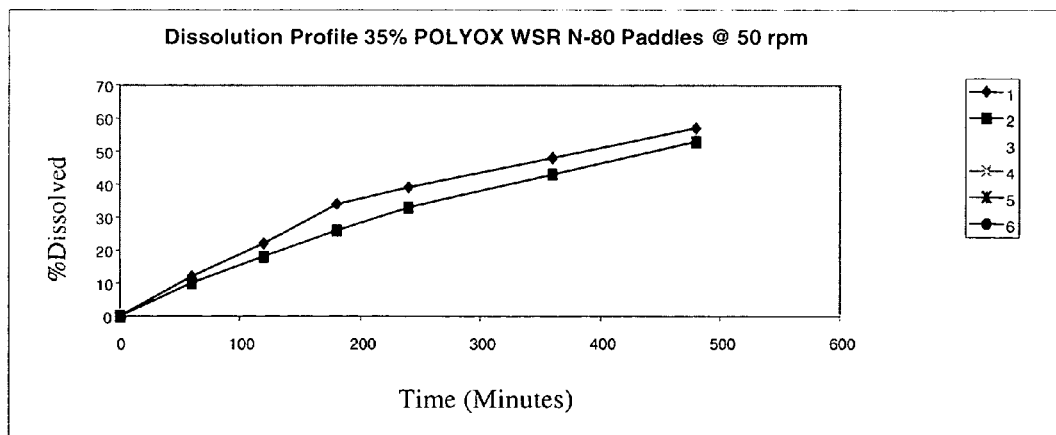

Figure 3b: Matrix Tablets from Example 1 with 25% polymer
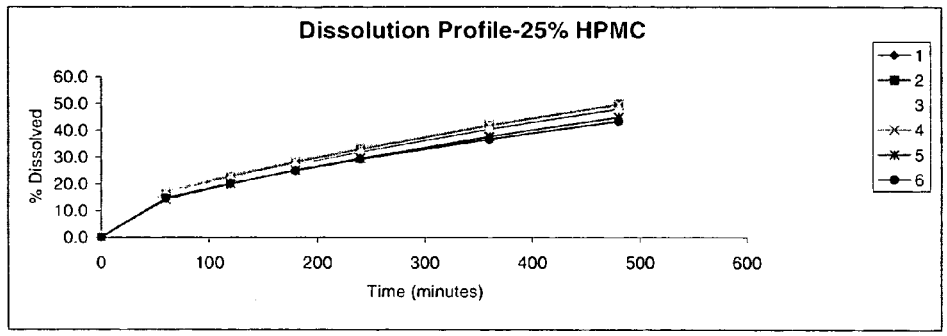
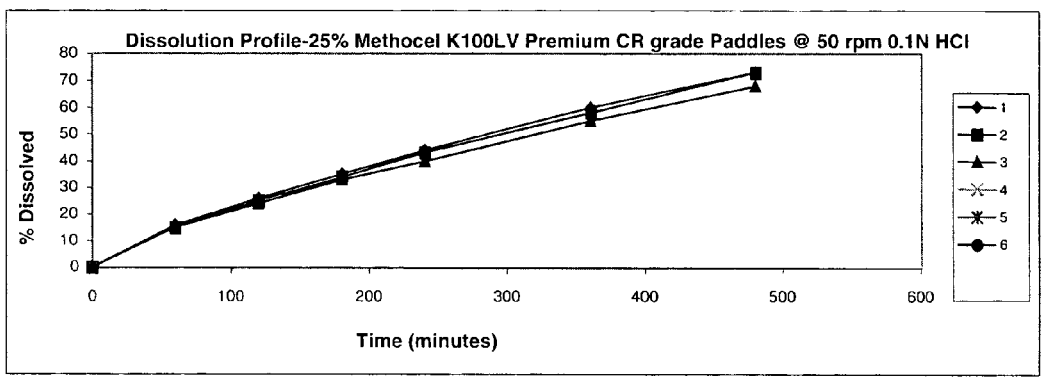
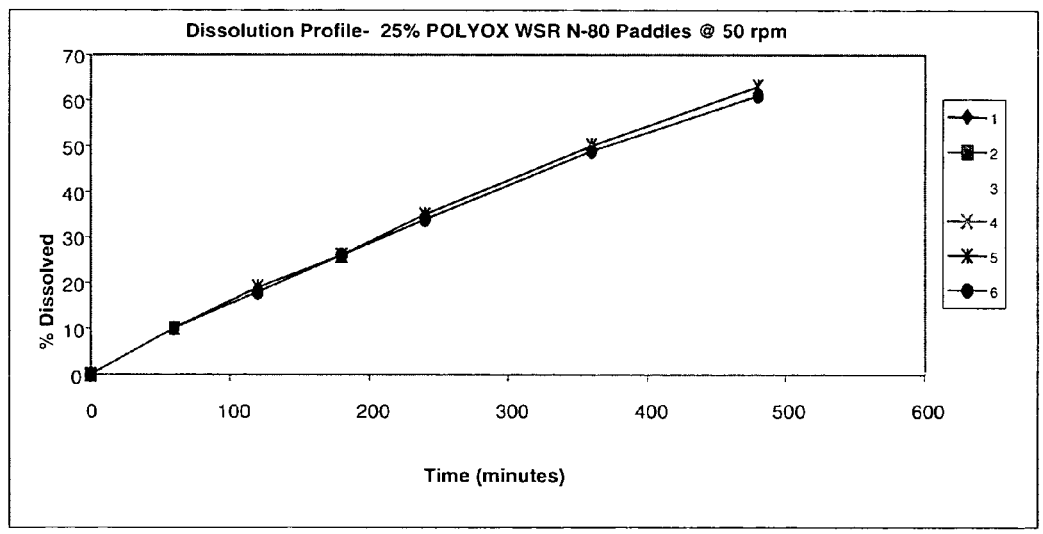

Figure 3c: Matrix tablets from Example 1 with 15% polymer
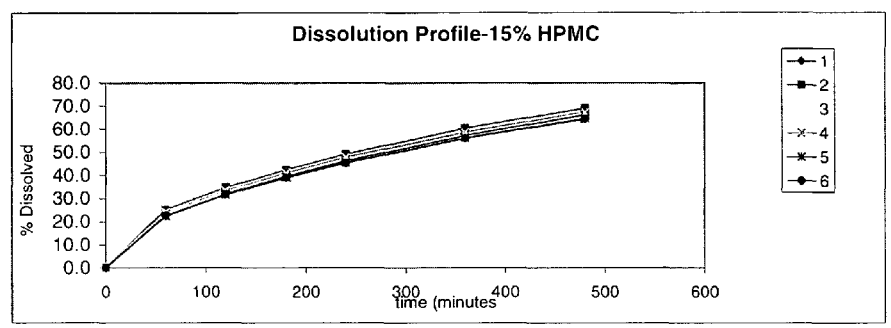
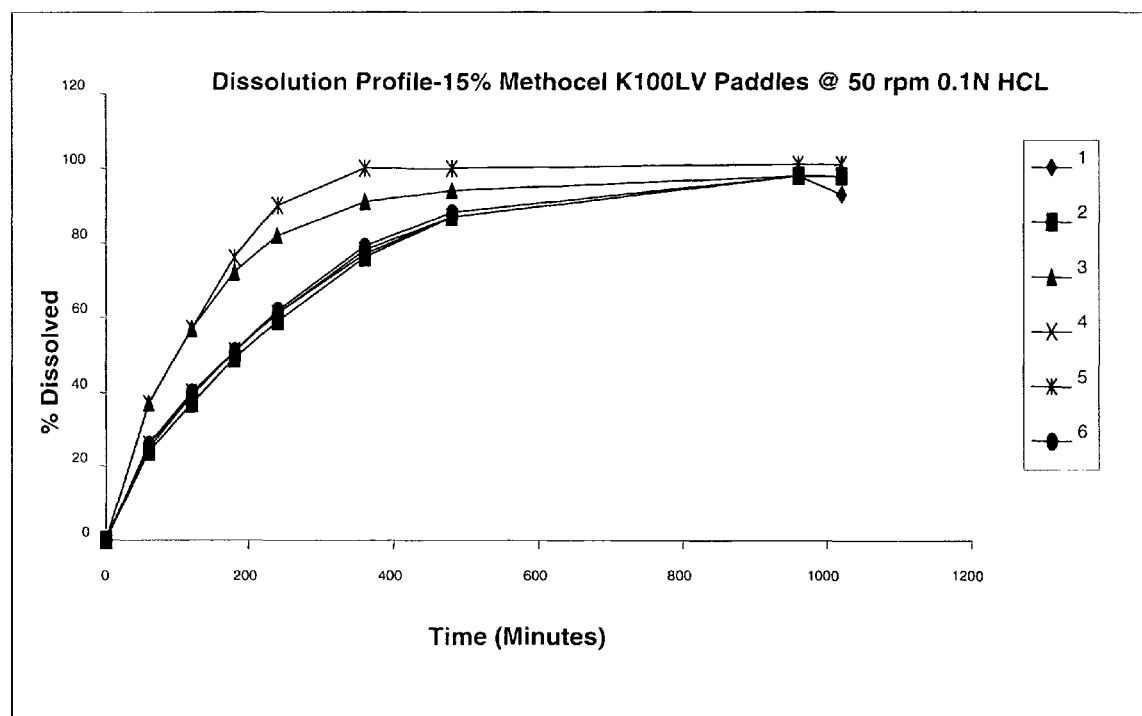

Figure 3d
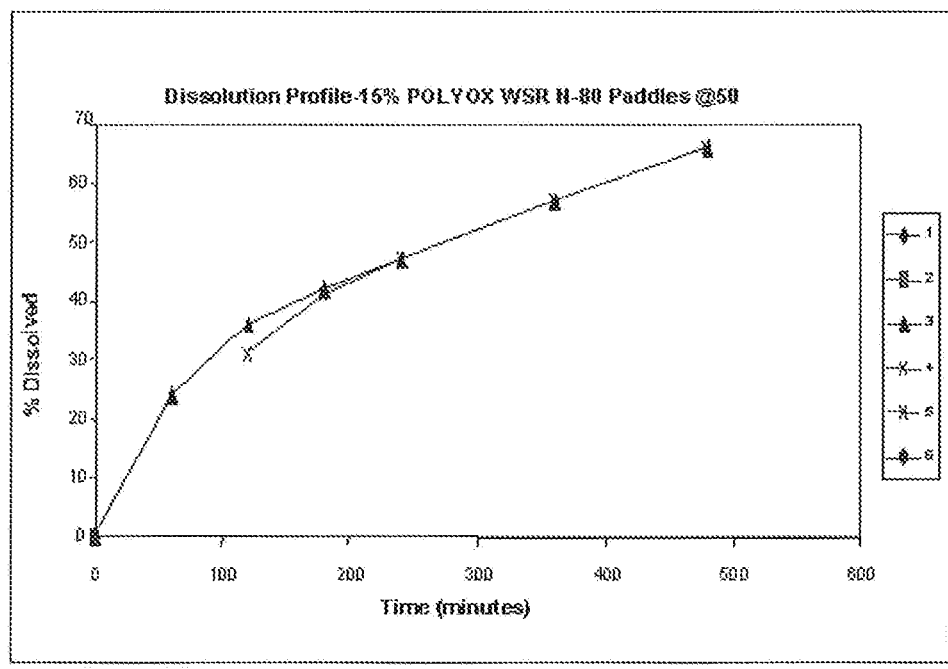
Figure 4. Dissolution profile from the matrix tablet of Example 2b.
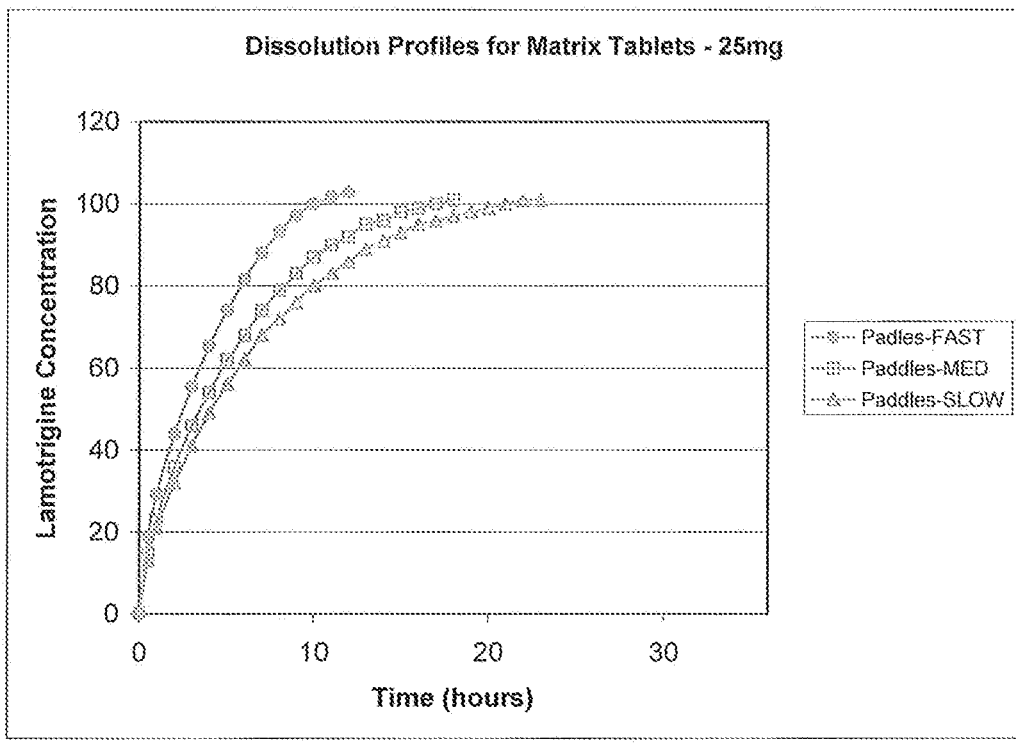

"Paddles" indicates the dissolution method, Fast/medium/slow indicate the release rates as set out in the table in Example 2b "Paddles" indicates the dissolution method, Fast/medium/slow indicate the release rates as set out in the table in Example 2b Figure 5: Dissolution Profile for tablets of Example 3 with 3% and 5% weight gain with a 80% Surelease, 20% Opadry coating.
Lamotrigine Sustained Release
80%Surelease 20% Opadry 3% weight gain
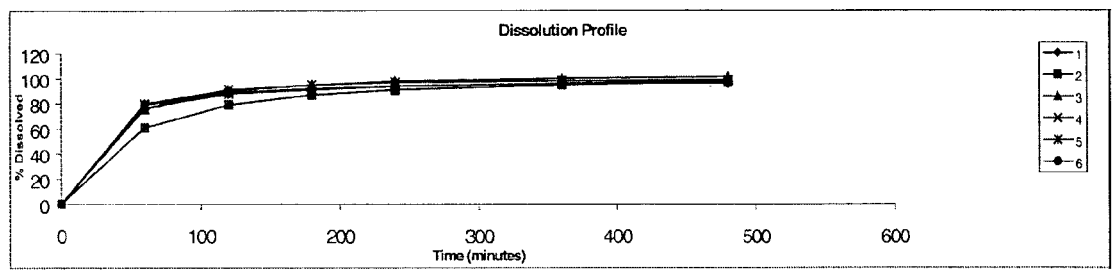
Lamotrigine Sustained Release
80% Surelease 20% Opadry 5 % weight gain
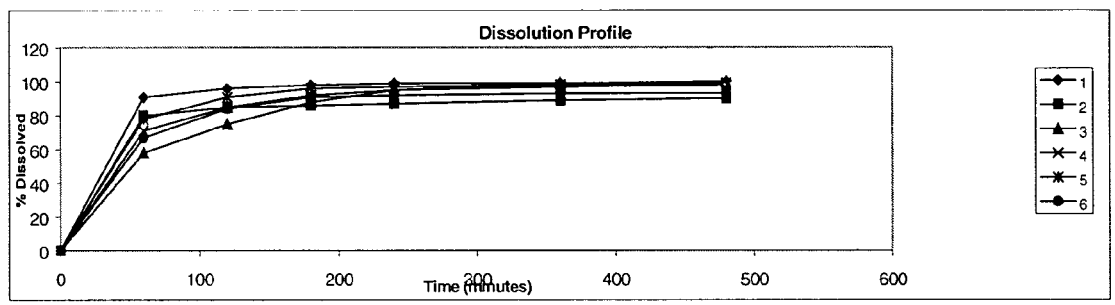

Figure 6: Dissolution profile of lamotrigine DiffCORE tablets 25 mg and 200mg of Example 4
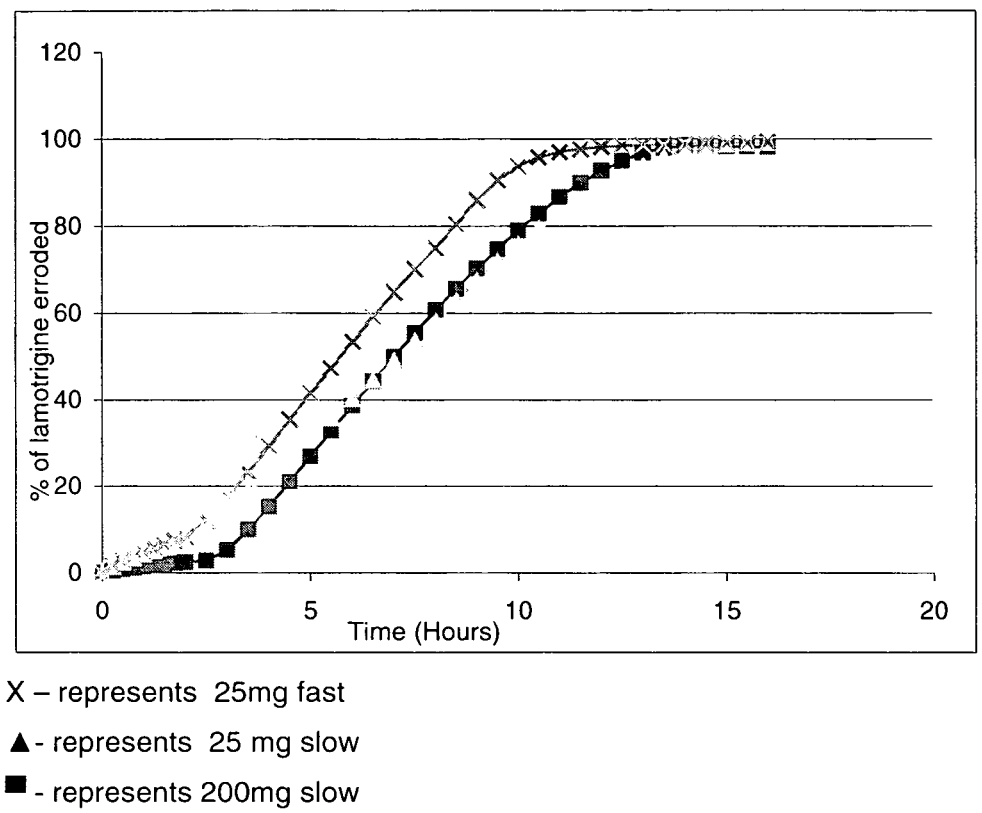
X – represents 25mg fast
▲ - represents 25 mg slow
■ - represents 200mg slow

Figure 7:

Serum lamotrigine Concentration over a 0 – 36 hour period for 25mg and 200mg matrix tablets of lamotrigine (Example 2) compared with the standard commercially available instant release (IR) tablets.

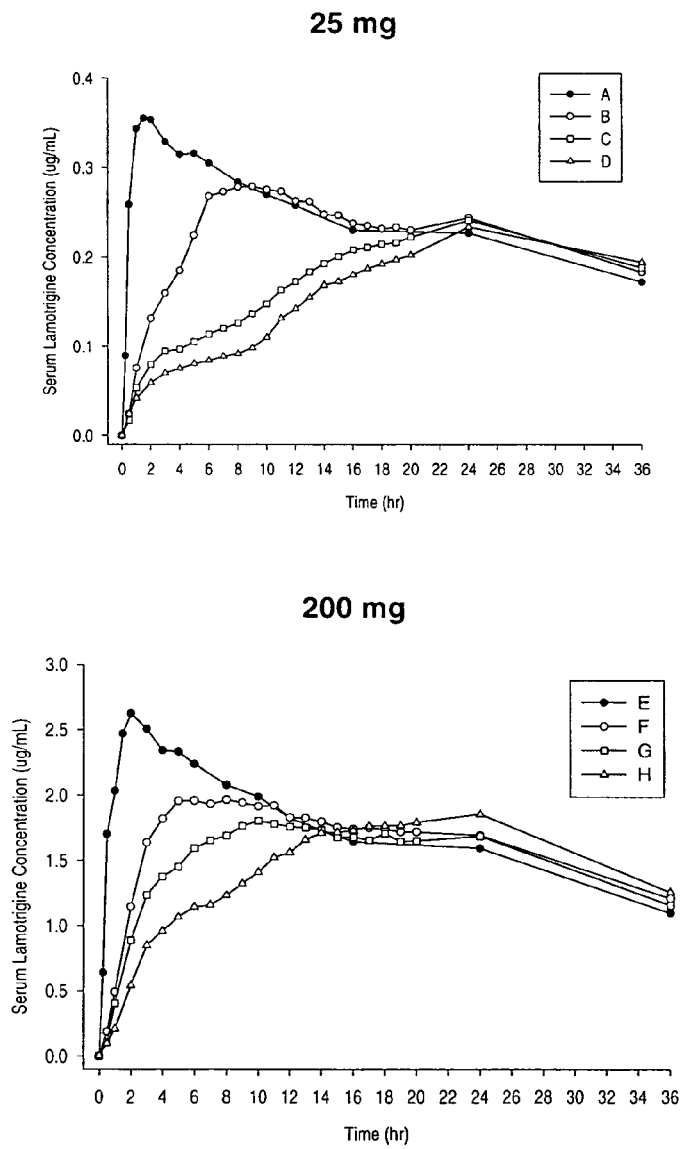

| A | LAMICTAL IR 25mg | E | LAMICTAL IR 200mg |
|---|---|---|---|
| B | LAMICTAL 25 mg matrix tablet - fast release –6 hour | F | LAMICTAL 200 mg matrix tablet – fast release - 6hr release rate |
| C | LAMICTAL 25mg matrix tablet - medium release rate - 12hr release rate | G | LAMICTAL 200mg matrix tablet – medium release rate -12hr release rate |
| D | LAMICTAL 25mg matrix tablet – slow – release rate - 16hr release rate | H | LAMICTAL 200mg matrix tablet – slow release rate- 16hr release rate |

Figure 8: Mean serum lamotrigine concentration-time profiles from the study of Example 7 for the 25mg tablets from Example 4.
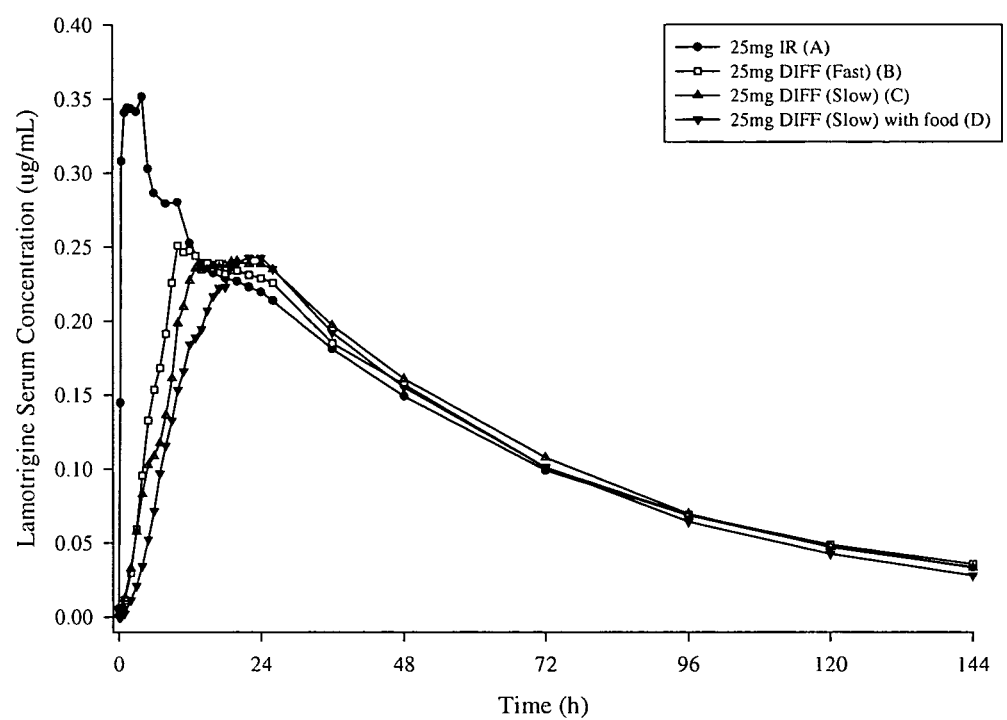

Figure 9 : 200mg IR profile from study outlined in Example 6 and profile of the 200mg DiffCORE tablets from Example 4 from study outlined in Example 7.
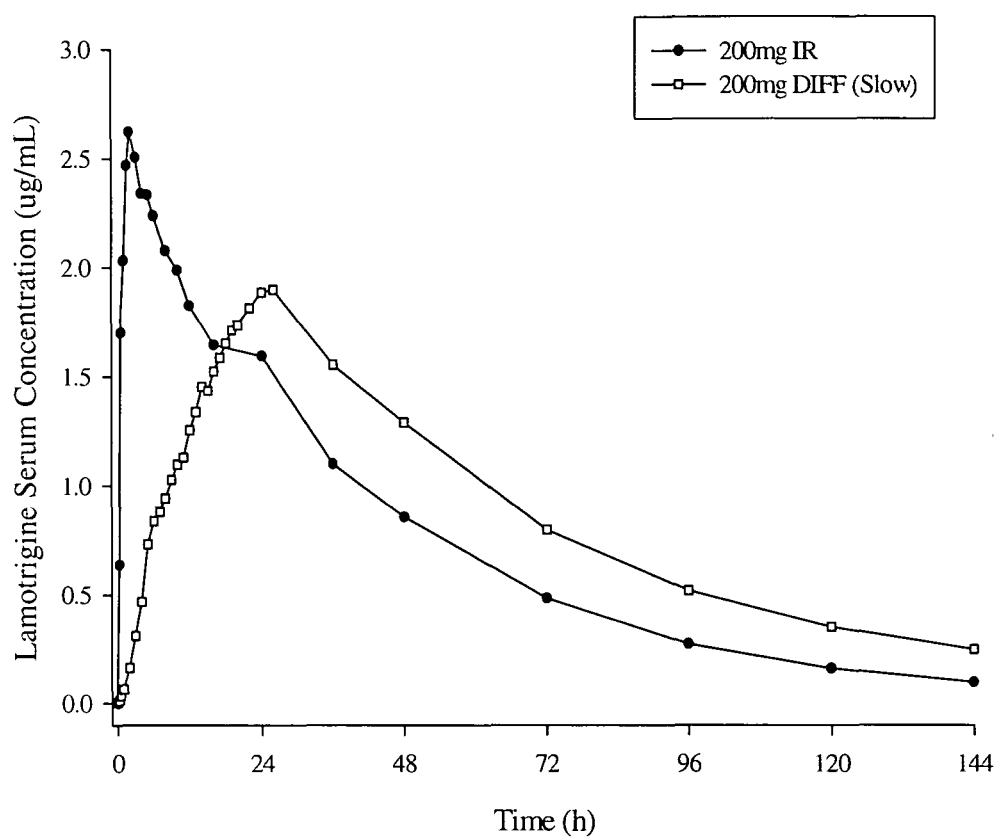

FORMULATIONS AND METHOD OF TREATMENT

This application, filed on 2 Dec. 2003, is a Continuation In Part of application Ser. No. 10/629,177, filed on 29 Jul., 2003, now abandoned, which claims priority from United Kingdom Patent Application Number 0217493.6, filed on 29 Jul. 2002, United Kingdom Patent Application Number 0217492.8, filed on 29 Jul. 2002, and United Kingdom Patent Application Number 0313801.3, filed on 13 Jun. 2003.

This invention relates to a novel method of treatment using lamotrigine and novel formulations, in particular tablet formulations, for use in such methods.

Lamotrigine, 3,5-diamino-6-(2,3-dichlorophenyl)-1,2,4-triazine is disclosed in U.S. Pat. No. 4,602,017 and EP0021121. Products comprising lamotrigine are marketed under the trade name LAMICTAL™ by the GlaxoSmithKline group of companies. Such products are particularly effective for treatment of CNS disorders, particularly epilepsy; pain; oedema; multiple sclerosis and psychiatric indications including bipolar disorder.

Various tablet formulations of lamotrigine have been approved for marketing, for instance, conventional compressed instant release (IR) tablets comprising 25 mg, 50 mg, 100 mg, 150 mg or 200 mg of active ingredient. These are administered once, twice or three times daily. For lamotrigine, added to an antiepileptic drug regime containing valproic acid, titration begins at 25 mg every other day for weeks 1 and 2 and increased to 25 mg every day for weeks 3 and 4. After this initial period the maintenance dose of 100 to 400 mg/day can be achieved by increasing the dose by 25 to 50 mg/day. If lamotrigine is added to enzyme-inducing antiepileptic drugs (EIAEDS) without valproic acid the dose is 50 mg/day for weeks 1 and 2 and 100 mg/day in 2 divided doses thereafter. To achieve the maintenance dose of 300 to 500 mg/day in 2 divided doses, doses may be increased by 100 mg/day every 1 to 2 weeks. These regimens provide a therapeutic amount of lamotrigine.

In addition, WO92/13527 (The Wellcome Foundation Limited) describes tablet formulations comprising water dispersible tablets comprising lamotrigine and a dispersing agent where the dispersing agent is a swellable clay such as a smectite and is generally present within the granules of the tablet to provide a tablet which is capable of dispersing in water within 3 minutes to provide a dispersion which will pass through a 710 μm sieve. The tablet can be optionally film coated in which case the dispersion time is less than 5 minutes. Chewable dispersible tablets which may be swallowed whole, chewed or dispersed in a small amount of water are marketed comprising 2 mg, 5 mg, 25 mg or 100 mg of active ingredient. These are generally administered to pediatric patients.

WO96/17611 (The Wellcome Foundation Limited) discloses pharmaceutical compositions comprising
   a) 0.5 to 50% by weight of lamotrigine;
   b) from 15 to 50% by weight lactose;
   c) from 15 to 50% by weight of starch;
   d) from 0.5 to 50% crystalline cellulose; and
   e) 5 to 15% by weight of polyvinylpyrrolidone;
and which is in the form of a free flowing powder having the following properties:
   (i) no granules having a particle size of greater than 850 μm,
   (ii) at least 90% by weight having a particle size of 75 to 850 μm,
   (iii) the granules disintegrate within 30 minutes according to the Disintegration Test of The Pharmacopoeia of Japan, 12th edition and
   (iv) at least 90% by weight of lamotrigine dissolves within 30 minutes when the granules are subjected to the Dissolution Test, method 2 (paddle method) of The Pharmacopoeia of Japan 12th edition 1991.

Lamotrigine is rapidly and completely absorbed after oral administration with negligible first pass metabolism. The absolute bioavailability is about 98%, which is not affected by food.

The chewable dispersible tablets were found to be equivalent to the lamotrigine compressed IR tablets whether they were administered as dispersed in water, chewed and swallowed or swallowed as whole in terms of rate and extent of absorption.

Other drugs available on the market for the treatment of epilepsy are, but not limited to, carbamazepine (Tegretol™), valproate (Depakote™), tiagabine (Gabitril™), levetiracetam (Keppra™), gabapentin (Neurontin™) and phenytoin (Dilantin™). Carbamazepine is available as an instant release tablet, a time releasing chewable tablet (Carbatrol; extended release beads) or Tegretol-XR an osmotic pump tablet, and a liquid to be administered by mouth. Valproate is available as an instant release tablet and a suspension. In the US valproate is also available as Depakote a delayed release (coated) tablet which contains sodium valproate+valproate in 1:1 formulation and also Depakote ER an extended release form). Gabapentin, tiagabine and levetiracetam are available as instant release tablets. Dilantin is available in a 'kapseal' that modifies release.

Existing marketed tablet formulations of lamotrigine provide immediate release of the active ingredients once the tablet reaches the stomach. The peak plasma concentrations occur anywhere from 1.4 to 4.8 hours following drug administration. The disadvantage is that the plasma concentration (pharmacokinetic profile (PK)) achieved with conventional tablets is cyclical, with peaks occurring after administration followed by troughs occurring before the next administration of drug, see FIG. (1).

In particular for the treatment of epilepsy it is speculated that the troughs may lead to breakthrough seizures and the peak plasma concentration may result in some adverse events (AE) occurring in some patients or alternatively the rate of increase in plasma concentration in the initial stages before the peak plasma concentration is achieved may also effect the AE profile.

Until recently, it was not known where, in the gastrointestinal tract, lamotrigine is absorbed. In carrying out a regional absorption study it has recently been discovered that the extent of absorption of lamotrigine is consistent when the drug is delivered to any point in the gastrointestinal tract between the stomach and the ascending colon. The extent of absorption is also equivalent whether the drug is delivered as a solid or as a solution.

Accordingly, in a first aspect, the invention comprises a sustained release formulation of lamotrigine or a pharmaceutically acceptable derivative thereof.

A further aspect of the present invention provides for a method of treating CNS disorders, which comprises orally administering to a patient a therapeutically effective amount of lamotrigine or a pharmaceutically acceptable derivative thereof in the form of a sustained release formulation.

A further aspect of the present invention provides for a method of treating CNS disorders, which comprises orally administering to a patient a therapeutically effective amount of lamotrigine or a pharmaceutically acceptable derivative thereof, in the form of a sustained release formulation wherein the lamotrigine or a pharmaceutically acceptable derivative thereof is released approximately 2 to 20 hours after administration, preferably 6 to 16 hours after administration and more preferably 10 to 15 hours, alternatively 10 to 14 hours after administration.

When used herein the term "CNS disorder" includes epilepsy; pain; oedema, multiple sclerosis, schizophrenia and psychiatric conditions including bipolar disorder, preferably epilepsy; pain; oedema, and psychiatric conditions including bipolar disorder, particularly epilepsy, pain and bipolar disorder.

When used herein the term "pain" includes acute pain such as musculoskeletal pain, post operative pain and surgical pain, chronic pain such as chronic inflammatory pain (e.g. rheumatoid arthritis and osteoarthritis), neuropathic pain (e.g. post herpetic neuralgia, trigeminal neuralgia, sympathetically maintained pain and pain associated with diabetic neuropathy) and pain associated with cancer and fibromyalgia or pain associated with migraine.

Schizophrenia is a serious psychiatric disease that affects 1% of the world's population. Onset of the disorder occurs typically in the late teens or early 20's and in approximately 80% of cases becomes a lifelong condition. Furthermore, schizophrenia is associated with significant mortality, with 40% of patients attempting suicide within 10 years of the onset of this disorder. The disorder was rated as the $5^{th}$ leading cause of disability in the US in a joint World Health Organisation—World Bank study in 1996 (Murray and Lopez, 1996).

The clinical presentation of schizophrenia can include positive symptoms, such as hallucinations, delusions, or thought disorder, and negative symptoms such as apathy, avolition, or poverty of speech.

The treatment of schizophrenia relies on the use of antidopaminergic drugs following the original discovery in the 1950's of the efficacy and mechanism of action of chlorpromazine. Chlorpromazine and other so-called "typical" antipsychotic drugs are still in common use today, though due to their association with motor side-effects, they are increasingly replaced by the newer "atypical" antipsychotics, such as clozapine (Clozaril™), olanzapine (Zyprexa™) or risperidone (Risperdal™). These newer drugs have a mixed pharmacology which includes dopamine D2 receptor antagonism and antagonism of the 5-HT2a receptor. Despite efficacy and relative safety of these newer drugs, a significant proportion of patients fail to respond to treatment and of those that do, many do not achieve a clinically meaningful improvement in global functioning and quality of life.

In some patients, episodes of major depression, mania, or mixed mania can occur alongside symptoms of schizophrenia. The distinction between schizophrenia and mood disorder is then somewhat blurred and a diagnosis of schizoaffective disorder is often used. Treatment of schizoaffective disorder typically requires a combination of an antipsychotic, an antidepressant, a mood stabiliser, and anxiolytic drugs. Although positive psychotic symptoms can usually be controlled, negative symptoms and affective symptoms are poorly treated by current medications.

Despite 40 years of development there remains a significant unmet need for treatment for patients with the chronic debilitating disorder schizophrenia.

Multiple sclerosis (MS) is an autoimmune disease which is a progressive disease of the central nervous system (CNS) in which patches of myelin (the protective covering of nerve fibres) in the brain and spinal cord are destroyed by the body's own immune system. This destruction leads to scarring and damage to the underlying nerve fibres and may manifest itself in a variety of symptoms, depending on the parts of the brain and spinal cord that are affected. Spinal cord damage may result in tingling or numbness as well as heavy and/or weak feeling in the extremities. Damage in the brain may result in muscle weakness, fatigue, unsteady gain, numbness, slurred speech, impaired vision, vertigo and the like. Leandri et al (J Neurol (2000) 247:556-558 reported that lamotrigine had been used in the treatment of trigeminal neuralgia secondary to multiple sclerosis.

A further aspect of the invention is the use of lamotrigine or a pharmaceutically acceptable derivative thereof in the treatment of multiple sclerosis.

A further aspect of the invention is a method of treatment of multiple sclerosis which comprises orally administering to a patient a therapeutically effective amount of lamotrigine or a pharmaceutically acceptable derivative thereof.

A further aspect of the invention is the use of lamotrigine or a pharmaceutically acceptable derivative thereof in the manufacture of a medicament for the treatment of multiple sclerosis.

When used herein the term "pharmaceutically acceptable derivative" means a salt, ester or salt of such ester which upon administration to the recipient such a human is capable of providing (directly or indirectly) lamotrigine or an active metabolite thereof. Preferred salts are inorganic acid salts such as hydrochloride, hydrobromide, phosphate or organic acid salts such as acetate, fumarate, xinafoate, tartrate, succinate or glutarate.

The term "treatment" as used herein includes the treatment of established disorders and also includes the prophylaxis thereof. This is particularly relevant for epilepsy wherein medication may treat seizures or prevent future seizures from occurring.

As used herein, the term "sustained release" refers to the gradual but continuous release over any extended period of lamotrigine after oral ingestion e.g. 2-20 hours preferably between 6 to 16 hours, and more preferably between 10 and 15 hours, alternatively 10 and 14 hours and which starts when the formulation reaches the stomach and starts to disintegrate/dissolve/erode. The release will continue over a period of time and may continue throughout the small intestine and after the formulation reaches the large intestine.

A further aspect of the invention provides a method of treating CNS disorders which comprises orally administering to a patient a therapeutically effective amount of lamotrigine in the form of a sustained release formulation wherein substantially all the lamotrigine is released from the formulation in the 2 to 20 hours after administration, preferably 6 to 16 hours after administration and more preferably 10 to 15, alternatively 10 to 14 hours after administration.

A further aspect of the invention provides a sustained release formulation of lamotrigine or a pharmaceutically acceptable derivative thereof, wherein substantially all the lamotrigine or a pharmaceutically acceptable derivative thereof is released from the formulation 2 to 20 hours after administration, preferably 6 to 16 hours after administration and more preferably 10 to 15, alternatively 10 to 14 hours after administration.

When used herein "substantially all" means more than 85%, preferably more than 90%.

Administration of lamotrigine over this time period delivers it gradually to the sites where lamotrigine is readily absorbed but with a slower rise in serum concentrations and reduced post-dosing peaks to mitigate dosing related adverse events (AE's) yet provide sufficient minimum plasma/serum concentrations (Cmin) to maintain efficacy. A formulation which achieves an area under the curve (AUC) equivalent to the conventional instant/immediate release (IR) tablet (90% confidence interval (CI) for the geometric least squares (GLS) mean ratio should fall within the range 80-125% compared to the reference IR product) is termed "bioequivalent".

Alternatively the sustained release formulation would not be deemed by the Food and Drug Administration (FDA) as bioequivalent to the IR tablets if the points estimate and the associated 90% Confidence Interval for Cmax will not fall within the limit of 80-125% relative to the IR product with the AUC remaining within the 80-125% range compared with the reference IR product.

Suitably the formulations are formulated such that the release of the active substance is predominantly in the stomach, small intestine and into the colon.

In a further aspect, the invention provides a method of treating CNS disorders, which comprises orally administering to a patient a therapeutically effective amount of lamotrigine or a pharmaceutically acceptable derivative thereof in the form of a sustained release formulation wherein the lamotrigine or a pharmaceutically acceptable derivative is present in the range of 1 to 500 mg, preferably 25 to 400 mg.

Preferably the sustained release formulation comprises an amount of lamotrigine or a pharmaceutically acceptable derivative selected from 25 mg, 50 mg, 100 mg, 200 mg or 400 mg.

Preferably the sustained release formulation is administered in a dosage regimen which is sufficient to maintain control over the disorder.

Preferably the dosage regimen is once a day.

An advantage of sustained release formulations is increased patient compliance.

Socio-economic factors do not influence compliance: non-compliance is just as likely in wealthy, well educated, and healthy patients as it is in patients outside these categories. In most cases, epilepsy is a life-long disease that requires consistent and adequate antiepileptic drug (AED) blood levels to maximize seizure control. Further, it is generally accepted that each additional seizure may increase the risk of recurrence and worsen the overall prognosis. Therefore, primary treatment objectives for patients with epilepsy are maintenance of adequate AED levels and prevention of subsequent seizures. Compliance with the prescribed dosing regimen is essential for the maintenance of therapeutic blood levels.

Patients with epilepsy often are treated with polypharmacy. Patients with severe or refractory epilepsy frequently require the co-administration of two or more AEDs to achieve adequate seizure control. Also, it is not unusual for patients to have other concurrent chronic medical conditions such as depression, heart conditions or diabetes that also require adherence to daily dosing regimens.

The treatment of bipolar disorder is currently recommended as once a day but the present formulation provides a lower rise in plasma concentration of the drug and thereby it is expected that this provides beneficial effects for the patient.

The availability of a once a day tablet for the treatment of pain would be a significant advantage, pain is a continuous disease state, therefore a sustained release formulation would provide pain relief by providing a Cmax at the appropriate point in the day or night depending when the patient's pain is most debilitating.

Preferably the formulation provides about a 10 to 40%, alternatively a 10 to 20% reduction in Cmax over the Cmax obtained in the same patient on an IR dose if administered once daily.

Preferably the formulation provides a time to Cmax ($t_{max}$) of 8 to 24 hours post dose, alternatively 10 to 16 hours post dose.

Preferably the formulation provides a rate of increase to $t_{max}$ of less than 50% of an individual IR dose.

The formulation may provide at 24 hours post dose a mean minimum serum concentration (Cmin) of at least 80 to 125% compared to the same IR dose in the same patient, or a (Cmin) higher that the IR dose and/or outside the range 80 to 125% compared to the same IR dose.

Preferably the formulation provides a fluctuation index (Cmax−Cmin/Cave) in the range of 0.15 to 0.45.

At present some patients, when administered the conventional IR tablets, experience CNS adverse event (AE's) such as dizziness, ataxia, diplopia and rash.

With the IR formulation the rate of AE's is for example, 31 to 38% dizziness, 10 to 22% ataxia and 24 to 28% diplopia. Without wishing to be bound by theory it is believed by the applicants that some of these adverse events relate to peak plasma levels or the rate of increase in plasma concentration after administration and before the peak plasma concentration is achieved. The risk of rash and of serious rash may be related to the initial dose or the rate of dose escalation of lamotrigine, and the development of a formulation that lowers the peak level during titration may lessen the risk of these adverse events.

A further aspect of the invention is a method of treating CNS disorders, which comprises orally administering to a patient a therapeutically effective amount of lamotrigine or a pharmaceutically acceptable derivative thereof in the form of a sustained release formulation, wherein a reduction in the AE's profile is achieved.

Preferably the reduction in the AE's profile is a reduction in the rate of an adverse event of at least one side effect selected from dizziness, ataxia, diplopia or rash.

Preferably the reduction in the AE's profile is a reduction in the rate of an adverse event of at least one side effect by 10%, preferably 20% more preferably 30%.

A further aspect of the invention is a method of reducing the incidence of at least one adverse event associated with the administration of lamotrigine or a pharmaceutically acceptable derivative thereof, which method comprises orally administering to a patient a therapeutically effective amount of lamotrigine or a pharmaceutically acceptable derivative in the form of a sustained release formulation.

Preferably the adverse event is at least one of dizziness, ataxia, diplopia or rash.

A further aspect of the invention is a method of treating epilepsy comprising orally administering to a patient a therapeutically effective amount of lamotrigine or a pharmaceutically acceptable derivative thereof in the form of a sustained release formulation.

A further aspect of the invention is the use of lamotrigine or a pharmaceutically acceptable derivative thereof in the treatment of CNS disorders for manufacture of a sustained release formulation as a means of treating epilepsy and reducing the rate of adverse events.

A further aspect of the invention is the use of lamotrigine or a pharmaceutically acceptable derivative thereof for manufacture of a sustained release formulation for the treatment of CNS disorders.

A further aspect of the invention is the use of lamotrigine or a pharmaceutically acceptable derivative thereof for manufacture of a sustained release formulation for the treatment of CNS disorders by any method described herein.

A further aspect of the invention is the use of lamotrigine or a pharmaceutically acceptable derivative thereof for the treatment of CNS disorders.

The dosage in a sustained release formulation intended to be swallowed whole where the dosage form integrity is essential for controlling the rate of release may conveniently be provided as a number of swallow tablets or capsules, for instance two, three or four. In cases where the release is achieved from a number of discrete particles, beads or granules, the dosage form need not be swallowed intact as long as the beads or particles themselves remain intact.

The dosage in a sustained release formulation may be also provided as a single tablet.

Preferably, a sustained release formulation of the present invention has an in vitro dissolution profile in which 40 to 65%, preferably 45 to 65%, more preferably 45 to 55% of the lamotrigine content is dissolved between 3 to 8 hours, more preferably between 4 to 6 hours; and that 90% of lamotrigine is dissolved between 6 and 16 hours, preferably between 10 to 15 alternatively 10 to 14 hours. In comparison, a conventional, immediate release lamotrigine tablet dissolves 80% within 30 minutes. The dissolution profile may be measured in a standard dissolution assay, for instance <724> Dissolution Test, Apparatus 1 or 2 or 3 or 4, provided in USP 24, 2000 and updated in subsequent supplements, at 37.0±0.5° C., using dilute hydrochloric acid or other suitable media (500-3000 ml) and a rotation speed of 50-100 rpm.

The sustained release formulation may provides an in vivo "Area Under the Curve" (AUC) value which is equivalent to that of the existing instant release IR tablet, for instance at least 80%, preferably at least 90% to 110%, more preferably about 100%, but not exceeding 125% of that of the corresponding dosage of lamotrigine taken as a conventional (immediate release) formulation, over the same dosage period, thereby maximising the absorption of lamotrigine from the sustained release formulation.

The pharmacokinetic profile for a dosage of the present invention may be readily determined from a single dosage bioavailability study in human volunteers. Plasma concentrations of lamotrigine may then be readily determined in blood samples taken from patients according to procedures well known and documented in the art.

The person skilled in the art will appreciate that a therapeutically effective amount will depend on the patient's age, size, severity of disease and other medication.

Preferred sustained release formulations are functional coated tablets or caplets, or time-release tablets or caplets matrices containing wax or polymer, or osmotic pump devices or combinations thereof. They can also be controlled release beads, granules, spheroids that are contained within a capsule or administered from a sachet or other unit dose powder device.

Representative sustained release formulations include a tablet, including swallow tablets, a capsule, granules or a sachet, typically a swallow tablet, which may or may not be coated.

A further aspect of the invention is a formulation comprising lamotrigine or a pharmaceutically acceptable derivative thereof and a release retarding excipient, which allows for sustained release of lamotrigine or a pharmaceutically acceptable derivative thereof. Suitable release retarding excipients include release-retarding polymers which may be swellable or not in contact with water or aqueous media such as the stomach contents; polymeric materials which form a gel on contact with water or aqueous media; polymeric materials which have both swelling and gelling characteristics in contact with water or aqueous media and pH sensitive polymers, for instance polymers based upon methacrylic acid copolymers such as the Eudragit (trade mark) polymers, for example Eudragit L (trade mark) which may be used either alone or with a plasticiser.

These sustained release formulations are often referred to in the art, as "matrix formulations" where by the drug is incorporated into a hydrated polymer matrix system and is released via diffusing or erosion, for example WO98/47491 and U.S. Pat. No. 5,242,627.

Release retarding polymers which may be swellable or not include, inter alia, cross-linked sodium carboxymethylcellulose, cross-linked hydroxypropylcellulose, hydroxyethylcellulose, high-molecular weight hydroxypropylmethylcellulose, carboxymethylamide, potassium methacrylatedivinylbenzene co-polymer, polymethylmethacrylate, cross-linked polyvinylpyrrolidone, hydroxyethyl cellulose high-molecular weight polyvinylalcohols etc.

Release retarding gellable polymers include methylcellulose, carboxymethylcellulose, low-molecular weight hydroxypropylmethylcellulose, hydroxyethyl cellulose, low-molecular weight polyvinylalcohols, polyoxyethyleneglycols, non-cross linked polyvinylpyrrolidone, xanthan gum etc.

Release retarding polymers simultaneously possessing swelling and gelling properties include medium-viscosity hydroxypropylmethylcellulose and medium-viscosity polyvinylalcohols.

Preferably the release retarding polymer used has a molecular weight in the range 5 to 95 thousand, more preferably in the range 10 to 50 thousand.

A preferred release-retarding polymer is one of the available grades of hydroxypropylmethyl cellulose or hydroxyethyl cellulose.

Examples of polymers which may be used include Methocel K4M (Trade Mark), Methocel E5M (Trade Mark), Methocel E50 (Trade Mark), Methocel E4M (Trade Mark), Methocel E100M (Trade Mark), Methocel K15M (Trade Mark), Methocel K100M (Trade Mark) and Methocel K100LV (Trade Mark), POLYOX WSR N-80 or mixtures thereof. Alternatively examples of polymers which may be used include Methocel K4M (Trade Mark), Methocel E5 (Trade Mark), Methocel E50 (Trade Mark), Methocel E4M (Trade Mark), Methocel K15M (Trade Mark), Methocel K100LV (Trade Mark), POLYOX WSR N-80 or mixtures thereof.

Other known release-retarding polymers which may be incorporated include hydrocolloids such as natural or synthetic gums, cellulose derivatives other than those listed above, carbohydrate-based substances such as acacia, gum tragacanth, locust bean gum, guar gum, agar, pectin, carageenin, soluble and insoluble alginates, carboxypolymethylene, casein, zein, and the like, and proteinaceous substances such as gelatine.

Preferably the release-retarding polymer is Methocel E4M Grade, POLYOX WSR N-80, Methocel K100LV.

The sustained release formulation may also include diluents/compression aid such as lactose, microcrystalline cellulose, dicalcium phosphate, sucrose, mannitol, xylitol; starches, and lubricants such as magnesium stearate, sodium stearyl fumarate and stearic acid. The sustained release formulation may further comprise disintegrants, such as cross-linked polyvinylpyrrolidone (CLPVP) and sodium starch glycollate; binders such as povidone (polyvinylpyrrolidone); flow aids such as silicon dioxide or talc. Typically, the sustained release formulation comprises from about 2.5 to 80% by weight of lamotrigine; from 0 to 70% by weight of diluent/compression aid and from 0.1 to 2.5% by weight of lubricant. Preferably the release retarding excipient is a release retarding polymer.

Preferably the release retarding polymer is present in a range of 10 to 70% by weight polymer.

Preferably the sustained release formulation comprises 2.5 to 80% by weight lamotrigine or a pharmaceutically acceptable derivative thereof.

Preferably the sustained release formulation comprises;
  a) 2.5 to 80% by weight lamotrigine or a pharmaceutically acceptable derivative thereof;
  b) 10 to 70% by weight release retarding polymer;
  c) 0 to 70% by weight diluent;
  d) 0 to 20% by weight compression aid; and
  e) 0.1 to 2.5% by weight lubricants.

In a preferred embodiment the sustained release formulation comprises
  a) 2.5 to 80% by weight lamotrigine or a pharmaceutically acceptable derivative thereof;
  b) 17.5 to 70% by weight release retarding polymer;
  c) 0 to 60% by weight diluent;
  d) 0 to 20% by weight compression aid; and
  e) 0.1 to 2.5% by weight lubricants.

In a preferred embodiment the sustained release formulation the compression aid is absent.

Preferably the sustained release formulation comprises
  a) 8.3 to 50% by weight lamotrigine or a pharmaceutically acceptable derivative thereof;
  b) 17.5 to 66.3% by weight release retarding polymer;
  c) 25 to 60% by weight diluent; and
  d) 0.1 to 0.4% by weight lubricant.

More preferably the sustained release formulation comprises
  a) 8.3 to 50% by weight lamotrigine or a pharmaceutically acceptable derivative thereof;
  b) 17.5 to 66.3% by weight Methocel E4MP, CR Grade, POLYOX WSRN-80 or Methocel, K100LV or a mixture thereof;
  c) 25 to 60% by weight lactose; and
  d) 0.1 to 0.4% by weight magnesium stearate.

A further aspect of the invention is a device comprising lamotrigine or a pharmaceutically acceptable derivative thereof and a release retarding coating on one or more of the outer surfaces of the device for example a tablet or a bead. A conventional instant release compression tablet may be at least partially coated by a release retarding coating or alternatively, a pharmaceutically acceptable bead is used in which the lamotrigine is incorporated and then the bead is at least partially coated by a release retarding coating. The use of beads allows flexibility in a dosage regimen because a dose can be measured to suit a patient's requirements.

The release retarding coating may be a film coat, which may be compression or spray dried, and may act as a semi permeable barrier thereby allowing diffusion control of drug release by water insoluble polymer, or a partially water-soluble polymer. Alternatively the film coating may control the dissolution rate. Such film coating may, for example, be composed of polymers which are either substantially or completely impermeable to water or aqueous media, or are slowly erodable in water or aqueous media or biological liquids and/or which swell in contact with water or aqueous media or biological liquids. Suitably the film coat should be such that it retains these characteristics at least until complete or substantially complete transfer of the active material content to the surrounding medium. Such film coated tablets are referred to as functional film coated tablets.

Suitable polymers for the film coat include acrylates, methacrylates, copolymers of acrylic acid or its esters, celluloses and derivatives thereof such as ethylcelluloses, cellulose acetate propionate, polyethylenes and polyvinyl alcohol etc. Film coats comprising polymers which swell in contact with water or aqueous media may swell to such an extent that the swollen layer forms a relatively large swollen mass, the size of which delays its immediate discharge from the stomach into the intestine. The film coat may itself contain lamotrigine, for example the film coat may be a slow or delayed release layer. Film coats may typically have an individual thickness of 2 microns to 10 microns.

Suitable polymers for film coats which are relatively impermeable to water include hydroxypropylmethyl cellulose polymers for example the Methocel (trade mark) series of polymers mentioned above, for example Methocel K100M, Methocel K15M; Eudragit (trade mark) polymers, Aquacoat (trade mark) and used singly or combined, or optionally combined with an Ethocel (trade mark) polymer. Alternatively and more preferred the film coat may be compressed. A preferred polymer is SURELEASE (trade mark) an aqueous ethylcellulose dispersion (E-7-19010). This can be obtained from COLORCON a division of Berwind Pharmaceuticals Services Inc. Additionally a mixture of SURELEASE polymer or other suitable partially permeable polymer and a pore forming material for example OPADRY (trade mark) clear (YS-2-7013), again which can be obtained from COLORCON, can be used. One range, which can be used, is 3 to 5% by weight of coating on a tablet.

Additional embodiments have a 50% to 80% by weight of film coating of SURELEASE polymer and 50% to 20% by weight of film coating of OPADRY.

A plasticiser such as hydrogenated castor oil may be combined with the polymer. The film coating may also include conventional binders, fillers, lubricants, colourants such as iron oxides or organic dyes and compression aids etc such as Polyvidon K30 (trade mark), magnesium stearate, and silicon dioxide, e.g. Syloid 244 (trade mark).

A further aspect of the invention is a sustained release formulation of lamotrigine or a pharmaceutically acceptable derivative thereof in which there are two phases in the release of lamotrigine or a pharmaceutically acceptable derivative thereof, wherein the release rate in the first phase is different from the release rate in the second phase. Preferably the release rate in the first phase will be slower than the release rate in the second phase. Most preferably in the first phase there is less than 15% release of lamotrigine or a pharmaceutically acceptable derivative thereof in the oesophagus and stomach and the second phase the release of lamotrigine or a pharmaceutically acceptable derivative thereof is at an increased rate than the first phase.

For example the first phase would be a period of on average 0 to 2 hours, and the second phase is 2 to 20 hours, preferably 2 to 16 hours, preferably 2 to 15 hours. It will be appreciated that in every patient the gastrointestinal timings can differ and therefore the 2 hours is an average across the patient population.

Preferably there is less than 10% release of lamotrigine or a pharmaceutically acceptable derivative thereof in the first phase.

This aspect of the invention is particularly advantageous as it reduces the release of lamotrigine in the stomach where the lamotrigine solubility is higher (compared to lower regions of the gastrointestinal tract). It may produce a substantially linear increase in plasma lamotrigine concentrations in vivo.

A further aspect of the invention is a sustained release formulation comprising;
  1) a core comprising lamotrigine or a pharmaceutically acceptable derivative thereof:
  2) an outer coating covering said core, the thickness of said outer coating being adapted such that it is substantially impermeable to the entrance of an environmental fluid and substantially impermeable to the exit of lamotrigine or a pharmaceutically acceptable derivative thereof, and 3) said outer coating including one or more orifices extending from the outside of the coating substantially completely through said coating but not penetrating said core allowing the release of lamotrigine or a pharmaceutically acceptable derivative thereof from the core into environmental fluid, said orifices having an area or combined area from about 10 to about 60 percent of the face area of said formulation, wherein the release lamotrigine or a pharmaceutically acceptable derivative thereof occurs substantially through said orifice.

Alternatively the sustained release formulation comprises;

1) a core comprising lamotrigine or a pharmaceutically acceptable derivative thereof;
2) an outer coating covering said core, the thickness of said outer coating being adapted such that it is impermeable or substantially impermeable to the entrance of an environmental fluid or exit of lamotrigine or a pharmaceutically acceptable derivative thereof during a dispensing period, and
3) said outer coating including one or more orifices extending from the outside of the coating substantially completely through said coating but not penetrating said core allowing the release of lamotrigine or a pharmaceutically acceptable derivative thereof from the core, said orifices having an area or combined area from about 10 to about 60 percent of the face area of said device, the rate limiting step for the release lamotrigine or a pharmaceutically acceptable derivative thereof substantially being the exit of lamotrigine or a pharmaceutically acceptable derivative thereof through said orifice via one or more of dissolution, diffusion or erosion of lamotrigine or a pharmaceutically acceptable derivative thereof in solution or suspension, said release retarding excipient enhancing or hindering the release of lamotrigine or a pharmaceutical acceptable derivative thereof depending upon the solubility and/or effective solubility of lamotrigine or a pharmaceutically acceptable derivative thereof in the environmental fluid.

Such sustained release devices are described in U.S. Pat. No. 5,004,614 which is incorporated herein in its entirety and referred to as "DiffCORE™ devices".

Preferably the core further comprises a release retarding excipient. More preferably the release retarding excipients are as described above for the matrix formulations.

Furthermore the outer coat may dissolve by 0.3 to 5 hours after administration or when the surrounding pH exceeds 5 preferably 5.5.

More preferably the core further comprises a release retarding excipient and the outer coat dissolves by 0.3 to 5 hours after administration or when the surrounding pH exceeds 5 preferably 5.5.

Preferably such formulations are comprised of a matrix core as described above and a outer coating including one or more orifices.

Preferably the release retarding excipient is as described above for matrix formulation.

Preferably the thickness of the outer coating is in the range 0.05 mm to 0.30 mm, preferably 0.10 mm to 0.20 mm.

Preferably the outer coat includes one or two orifices.

Preferable the outer coating is selected from the group consisting of ethyl cellulose, acrylate polymers, polyamides, polymethacrylates, waxes, polyanhydrides, polyglycolides, polyactides, polybutyrates, polyvalerates, polycaprolactones, natural oils, polydimethylsiloxane, cross-linked or uncrossed linked sodium carboxymethylcellulose starch, polyvinylpyrollidone, cellulose ethers, cellulose acetate phthalate, polyvinylalcohol phthalate, shellac, zein, hydroxypropylmethyl cellulose phthalate, methacrylic acid polymers or copolymers, one or more of the above and the like.

Preferably the formulation comprises; 2.5 to 80% by weight lamotrigine or a pharmaceutically acceptable derivative thereof.

In a preferred embodiment the sustained release formulation comprises a core comprising
   a) 2.5 to 80% by weight lamotrigine or a pharmaceutically acceptable derivative thereof;
   b) 17.5 to 70% by weight release retarding polymer;
   c) 0 to 60% by weight diluent;
   d) 0 to 20% by weight compression aid; and
   e) 0.1 to 2.5% by weight lubricants and
   an outer coat comprising
   f) 0.05 mm to 0.30 mm of polymer;

In a preferred embodiment of the sustained release formulation, the compression aid is absent.

In a more preferred embodiment the sustained release formulation comprises a core comprising
   a) 5 to 66% by weight lamotrigine or a pharmaceutically acceptable derivative thereof;
   b) 17.5 to 66.3% by weight release retarding polymer;
   c) 0 to 60% by weight diluent; and
   d) 0.1 to 0.4% by weight lubricants;
   and an outer coat comprising
   e) 0.05 mm to 0.30 mm of polymer.

Preferably the release retarding polymer is a HPMC polymer, more preferably it is selected from Methocel E4M, CR Grade, POLYOX WSRN-80 or Methocel K100LV, or a mixture thereof.

Preferably the outer coat polymer is a methacrylic acid copolymer, more preferably Eudragit.

Preferably the lamotrigine or a pharmaceutically acceptable derivative thereof is present in an amount 5 to 55%.

More preferably the sustained release formulation comprises a core comprising:
   a) 5 to 55% by weight lamotrigine or a pharmaceutically acceptable derivative thereof;
   b) 17.5 to 66.3% by weight Methocel E4MP, CR Grade, POLYOX WSRN-80 or Methocel, K100LV or a mixture thereof;
   c) 25 to 60% by weight lactose; and
   d) 0.1 to 0.4% by weight magnesium stearate;
   and an outer coat comprising
   e) 0.05 mm to 0.30 mm of Eudragit L30.

"Environmental fluid" means the fluid present or mimic the dissolution properties of that in a patient's gastrointestinal tract.

"Dispensing period" means from the time of administration to the end of the release of lamotrigine or the pharmaceutically acceptable derivative thereof e.g. 0 to 20 hours, preferably 0 to 16 hours, more preferably 0 to 15 alternatively, 0 to 14 hours.

When used herein in "substantially impermeable" means that little or no lamotrigine or a pharmaceutically acceptable derivative thereof is allowed to egress through the coat e.g. less than less than 5%, preferably less than 2% even more preferably less than 1% or that little or no environmental fluid is allowed to ingress through the coat e.g. less than less than 5%, preferably less than 2% even more preferably less than 1%

When used herein the term "orifice" means an aperture in the outer coat, for example an opening in the outer coat of the tablet and include a portion of the surface of the outer coat which is significantly thinner that the remainder of the coat for example.

When used herein the term "release" means, the exiting of lamotrigine or a pharmaceutically acceptable derivative thereof from the formulation into environmental fluid for example by dissolution, diffusion, osmosis or erosion.

Matrix tablets as described above can be compression or spray coated with an aqueous solution of polymer to produce a film coat. Coating can take place in any standard coating machine known to the person skilled in the art, for example a Vector™ machine. The orifice or orifices are then drilled into the tablet film coat. The orifices can be produced by removing certain portion(s) of the film coat from the previously coated tablet surface.

Typically the surface area removed is between 0.1% to 50%, preferably around 15-20%. The orifices can be produced by mechanical drilling, ultrasonic cutting or laser, mechanical drilling is preferred.

The orifices can be any shape, for example oval, round, square or even shaped as text, for example a company logo, preferably the orifice is round The orifice size will depend on the size of the tablet but for example can be 0.1 to 6-7 mm for 9-10 mm tablet, preferably 4-4.5 mm.

If the tablet has more than one orifice, the orifices can be on the same or difference faces of the tablets, preferably on opposite faces.

The orifice can be centred on the face of the tablet or off centre.

Tablets may be round, oval, elliptical, shield or capsule shape, shallow to deep convex. Preferably the tablet is round or oval shaped, standard convex.

A further aspect of the invention is a formulation comprising lamotrigine or a pharmaceutically acceptable derivative thereof and an osmotic agent which is coated with a water permeable membrane containing at least one hole. The active ingredient is "pumped" out of the tablet through the hole in the water permeable membrane. Examples of osmotic pump formulations of other drugs are contained in WO95/29665.

A further particular aspect of the invention provides a system for the sustained release of lamotrigine or a pharmaceutically acceptable derivative thereof, comprising (a) a deposit-core comprising an effective amount of the active substance and having defined geometric form, and (b) a support-platform applied to said deposit-core, wherein said deposit-core contains at least the active substance, and at least one member selected from the group consisting of (1) a polymeric material which swells on contact with water or aqueous liquids and a gellable polymeric material wherein the ratio of the said swellable polymeric material to said gellable polymeric material is in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids.

Such systems can be referred to as "Procise technology".

The support-platform may comprise polymers such as hydroxypropylmethylcellulose, plasticizers such as a glyceride, binders such as polyvinylpyrrolidone, hydrophilic agents such as lactose and silica, and/or hydrophobic agents such as magnesium stearate and glycerides. The polymer(s) typically make up 30 to 90% by weight of the support-platform, for example about 35 to 40%. Plasticizer may make up at least 2% by weight of the support-platform, for example about 15 to 20%. Binder(s), hydrophilic agent(s) and hydrophobic agent(s) typically total up to about 50% by weight of the support-platform, for example 40 to 50%.

Tablet formulations of the invention may contain a waxy or similar water insoluble material in order to form the matrix. Such a tablet may be formed by dry blending the drug and any diluent materials with the waxy material in particulate form. Examples of suitable waxy materials are cetyl alcohol, stearyl alcohol, palmitoyl, alcohol, oleyl alcohol and carnuba wax. There resulting blend is then compressed into tablets using conventional tablet making technologies. An alternative methods of manufacturing these tablets would be to granulate the drug with the diluent materials with a suitable volatile granulating fluid (water, ethanol, isopropanol) and to dry the granules, then coat them with a molten waxy material. The resultant granules are then compressed into tablet using conventional tablet making technology.

Granule based tablets can also be made by spraying a solution or suspension of one of the methacrylate based release controlling agents (Eudragit—trade mark) onto a blend of the drug mixed with one of the common diluents. Examples of suitable Eudragits are NE30D, L, S. The granules formed in the process are then dried and compressed using conventional tablet making technology.

The tablet formulations of the invention may be wholly or partly covered by a coating layer, which may be a protective layer to prevent ingress of moisture or damage to the tablet. The protective layer may itself contain active material content, and may, for example, be an immediate release layer, which immediately disintegrates in contact with water or aqueous media. Preferred materials for the protective layer are hydroxypropylmethylcellulose and polyethylene glycol, with titanium dioxide as an opacifying agent, for instance as described in WO 95/28927 (SmithKline Beecham).

As well as active material content etc, the tablet of the invention may also include a pH modifying agent, such as a pH buffer. A suitable buffer is calcium hydrogen phosphate.

The protective layer, if present, may typically be made up by a wet granulation technique, or by dry granulation techniques such as roller compaction. Typically the protective layer material, e.g. Methocel (trade mark) is suspended in a solvent such as ethanol containing a granulation acid such as Ethocel or Polyvidon K-30 (trade mark), followed by mixing, sieving and granulation. Typically a first layer may be formed, then a barrier layer deposited upon it, e.g. by compression, spraying or immersion techniques, then the second layer may be formed so that the barrier layer is sandwiched between the first and second layers. Additionally, or alternatively, the first and second layers may be formed and a barrier layer may then be formed, for instance by compression, spraying or immersion, on one or more of the end faces of the tablet.

Chewable tablets according to the present invention typically comprise a chewable base formed from, for instance, mannitol, sorbitol, dextrose, fructose, lactose, xylitol, maltitol, sucrose, or galactose alone or in combination. A chewable tablet may also comprise further excipients, for instance, disintegrants, lubricants, sweetening agents, colouring and flavouring agents. Such further excipients together will preferably comprise from 3 to 10%, more preferably 4 to 8%, yet more preferably 4 to 7% by weight of the tablet. Disintegrants may be present in from 1 to 4%, preferably from 1 to 3%, more preferably from 1 to 2% by weight of the tablet. Representative disintegrants include crospovidone, sodium starch glycollate, starches such as maize starch and rice starch, croscarmellose sodium and cellulose products such as microcrystalline cellulose, microfine cellulose, low substituted hydroxy propyl cellulose, either used singly or in admixture. Preferably, the disintegrant is crospovidone. Lubricants may be present in from 0.25 to 2.0%, preferably from 0.5 to 1.2% by weight of the tablet. Preferred lubricants include magnesium stearate. Preferably, the sweetening agent is an artificial sweetening agent such as sodium saccharin or aspartame, preferably aspartame, which may be present in from 0.5 to 1.5% by weight of the tablet. Preferably, a tablet of the present invention is substantially free of sugar (sucrose). Preferred flavouring agents include fruit flavours which may be natural or synthetic, for instance peppermint, cherry and banana, or a mixture thereof.

Single dose sachets according to the present invention comprise, in addition to the drug substance, excipients typically included in a sachet formulation, such as a sweetener, for instance aspartame, flavourings, for instance fruit flavours, optionally a suspending agent such as xanthan gum, as well as silica gel, to act as a desiccant.

Capsules according to the present invention comprise, in addition to the drug substance, excipients typically included in a capsule, for instance starch, lactose, microcrystalline cellulose, ethyl cellulose, magnesium stearate. Preferably, capsules are prepared from materials such as HPMC or a gelatine/PEG combination. Preferably the capsules will contain beads or granules. These beads or granules are composed of the drug substance in a concentration of between 5% and 95%, preferably 20 to 80%, most preferably 50 to 80%. The drug substance is mixed with a suitable granulating aid such as microcrystalline cellulose, lactose, and granulated using a suitable granulating fluid such as water, ethanol and/or isopropanol. The wet granules are forced through small orifices of 0.5 mm to 3 mm diameter then spheronised into discrete particles using a rapidly spinning disc. The spherical particles are then dried and coated with a release controlling film coat containing for example ethyl cellulose, pH sensitive or insensitive methacrylic acid copolymers and their derivatives. The coated particles are filled into suitable capsule shells.

Preferably, the unit dosage forms of the present invention are packaged in containers that inhibit the ingress of atmospheric moisture, for instance blister packs, tightly closed bottles or desiccated pouch packs etc which are conventional in the art. Preferred bottles include HDPE bottles.

Other sustained release formulations which may be suitable for incorporating lamotrigine or other suitable derivatives thereof are described in:

Sustained Release Medications, Chemical Technology Review No. 177. Ed. J. C. Johnson. Noyes Data Corporation 1980.

Controlled Drug Delivery, Fundamentals and Applications, 2nd Edition. Eds. J. R. Robinson, V. H. L. Lee. Mercel Dekkes Inc. New York 1987.

Examples of delayed release formulations which are suitable for incorporating lamotrigine or other suitable derivatives thereof are described in:

Remington's Pharmaceutical Sciences 16th Edition, Mack Publishing Company 1980, Ed. A. Osol.

A further aspect of the invention is a sustained release formulation of the invention additionally containing a second active ingredient selected from carbamazepine, valproic acid, gabapentin, diazepam, phenytoin, bupropion or paroxetine HCl.

Preferably both the lamotrigine and the second active ingredient are both administered in a sustained release fashion. Alternatively the formulation contains 2 phases, one sustained release phase comprising lamotrigine and a second instant release phase comprising the second active ingredient.

The invention will now be described by way of example only, with reference to the accompanying drawings, in which:

FIG. 1. Simulated lamotrigine pharmacokinetic profile for 200 mg lamotrigine IR tablets administered twice daily.

FIG. 2. Dissolution profile of three different batches of lamotrigine 150 mg IR tablets.

FIG. 3(a-d). Dissolution profiles from a matrix tablet from Example 1.

FIG. 4-4a. Dissolution profiles from a matrix tablet from Example 2.

FIG. 5. Dissolution profiles from a film coated tablet from Example 3. FIG. 5 shows the dis FIG. 6. Dissolution profile of lamotrigine DiffCORE tablets 25 mg and 200 mg of Example 4.

FIG. 7. Serum lamotrigine concentrations over 0-36 hour for 25 mg and 200 matrix tablets of lamotrigine (Example 2) compared with the standard IR tablets.

Figure 8A:
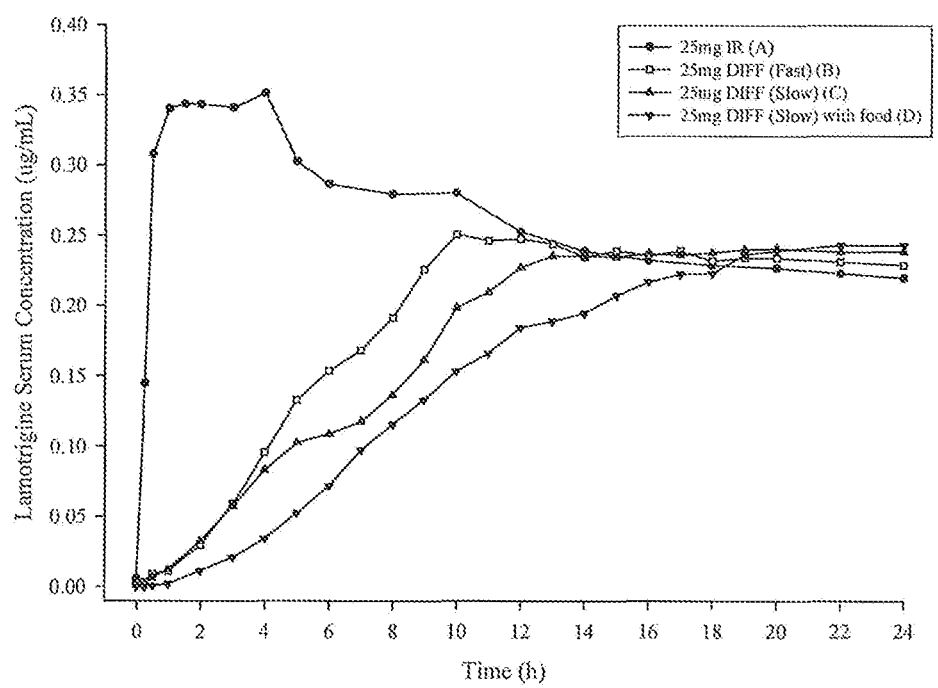

FIG. 8-8a. Mean serum lamotrigine concentration-time profiles from the study of Example 7 for the 25 mg tablets from Example 4.

FIG. 9. 200 mg IR profile from study outlined in Example 6 and the profile of 200 mg lamotrigine DiffCORE tablet of Example 4 from study outlined in Example 7.

A further aspect of the invention is a sustained release formulation of lamotrigine or a pharmaceutically acceptable derivative thereof which has an in vitro dissolution profile substantially similar to the dissolution profile shown in FIG. 3, 4, 5 or 6.

A further aspect of the invention is a sustained release formulation of lamotrigine or a pharmaceutically acceptable derivative thereof which has an in vivo dissolution profile substantially similar to profiles shown in any one of FIG. 7, 8 or 9.

The present invention also extends to formulations which are bioequivalent to the tablets or formulations of the present invention, in terms of both rate and extent of absorption, for instance as defined by the US Food and Drug Administration and discussed in the so-called "Orange Book" (Approved Drug Products with Therapeutic Equivalence Evaluations, US Dept of Health and Human Services, 19th edn, 1999).

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Example 1

Matrix Formulations

Example 1a

Matrix Tablets with 35% Polymer (Polymers are either Methocel E4MP CR, Methocel K100 LV or Polyox WSR N-80)

| Component | Quantity (mg/tablet) | Quantity (% w/w) |
|---|---|---|
| Lamotrigine | 150 | 30.0 |
| Lactose (Fast-Flo) | 35 | 7.0 |
| Microcrystalline cellulose | 138 | 27.6 |

-continued

| Component | Quantity (mg/tablet) | Quantity (% w/w) |
|---|---|---|
| Polymer | 175 | 35.0 |
| Magnesium Stearate | 2 | 0.4 |
| Total Tablet Weight | 500 | 100 |

Bulk Preparation Method

First the components were weighed from bulk containers in the following amounts:

| Ingredients | Amount (G) |
|---|---|
| Lamotrigine | 450.0 |
| Lactose (Fast-Flo) | 105.0 |
| Microcrystalline cellulose | 414.0 |
| Polymer | 525.0 |
| Magnesium Stearate | 6.0 |

The components were then sieved using a Russel-SIV equipped with a 20-mesh (850 μm) or an equivalent sieve and mesh, and deposited into a stainless-steel blending container.

The lamotrigine, lactose, microcrystalline cellulose and polymer were blended for 15 minutes using a suitable blender, such as a Matcon-Buls bin-type blender, a V-blender or equivalent. The magnesium stearate was added to the mixture and blending continued for approximately 2 minutes.

The lubricated blend was compressed using a suitable rotary tablet press, typically a Fette 2090 or equivalent. In-process controls for tablet weight and hardness were applied at appropriate intervals throughout the compression run and adjustments to the tablet press were made as necessary.

Example 1b

Matrix Tablets with 25% Polymer (Polymers are either Methocel E4MP CR, Methocel K100 LV or Polyox WSR N-80)

| Component | Quantity (mg/tablet) | Quantity (% w/w) |
|---|---|---|
| Lamotrigine | 150 | 30.0 |
| Lactose (Fast-Flo) | 85 | 17.0 |
| Microcrystalline cellulose | 138 | 27.6 |
| Polymer | 125 | 25.0 |
| Magnesium Stearate | 2 | 0.4 |
| Total Tablet Weight | 500 | 100 |

Bulk Preparation Method

First the components were weighed from bulk containers in the following amounts:

| Ingredients | Amount (G) |
|---|---|
| Lamotrigine | 450.0 |
| Lactose (Fast-Flo) | 255.0 |
| Microcrystalline cellulose | 414.0 |
| Polymer | 375.0 |
| Magnesium Stearate | 6.0 |

The components were then sieved using a Russel-SIV equipped with a 20-mesh (850 μm) or an equivalent sieve and mesh, and deposited into a stainless-steel blending container.

The lamotrigine, lactose, microcrystalline cellulose, and polymer were blended for 15 minutes using a suitable blender, such as a Matcon-Buls bin-type blender, a V-blender or equivalent. The magnesium stearate was then added to the mixture and blending was continued for approximately 2 minutes.

The lubricated blend was then compressed using a suitable rotary tablet press, typically a Fette 2090 or equivalent. In-process controls for tablet weight and hardness were applied at appropriate intervals throughout the compression run and adjustments to the tablet press were made as necessary.

Example 1c

Matrix Tablets with 15% Polymer (Polymers are either Methocel E4MP CR, Methocel K100 LV or Polyox WSR N-80)

| Component | Quantity (mg/tablet) | Quantity (% w/w) |
|---|---|---|
| Lamotrigine | 150 | 30.0 |
| Lactose (Fast-Flo) | 35 | 7.0 |
| Microcrystalline cellulose | 238 | 47.6 |
| Polymer | 75 | 15.0 |
| Magnesium Stearate | 2 | 0.4 |
| Total Tablet Weight | 500 | 100 |

Bulk Preparation Method

First the components were weighed from bulk containers in the following amounts:

| Ingredients | Amount (G) |
|---|---|
| Lamotrigine | 450.0 |
| Lactose (Fast-Flo) | 105.0 |
| Microcrystalline cellulose | 714.0 |
| Polymer | 225.0 |
| Magnesium Stearate | 6.0 |

The components were then sieved using a Russel-SIV equipped with a 20-mesh (850 μm) or an equivalent sieve and mesh, and deposited into a stainless-steel blending container.

The lamotrigine, lactose, microcrystalline cellulose and polymer were blended for 15 minutes using a suitable blender, such as a Matcon-Buls bin-type blender, a V-blender or equivalent. The magnesium stearate was then added to the mixture and blending was continued for approximately 2 minutes.

The lubricated blend was then compressed using a suitable rotary tablet press, typically a Fette 2090 or equivalent. In-process controls for tablet weight and hardness were applied at appropriate intervals throughout the compression run and adjustments to the tablet press are made as necessary.

Example 2a

Matrix Formulations

| | Strength | | | | | | | |
|---|---|---|---|---|---|---|---|---|
| | 25 mg | | 50 mg | | 100 mg | | 200 mg | |
| Excipient | Slow | Fast | Slow | Fast | Slow | Fast | Slow | Fast |
| Lamotrigine | 25 mg (12.5%) | 25 mg (12.5%) | 50 mg (25%) | 50 mg (25%) | 100 mg (33.3%) | 100 mg (33.3%) | 200 mg (50%) | 200 mg (50%) |
| E4M | 55.75 | 20% | 30% | 10% | 25% | 2.5% | 15% | 5% |
| K100LV | 9.75 | 20% | 20% | 25% | 10% | 25% | 5% | 15% |
| Lactose* | qs | Qs | qs | q.s. | qs | qs | qs | qs |
| Mg Stearate | 0.4% | 0.4% | 0.4% | 0.4% | 0.4% | 0.4% | 0.4% | 0.4% |
| Tablet Weight (mg) | 300 | 300 | 325 | 325 | 350 | 350 | 400 | 400 |

*qs = the mass balance to achieve the target tablet weight

In the above table slow represents tablets where 90% of the lamotrigine dissolved in vitro in 16 hours, fast represents 90% of the lamotrigine dissolved in 6 hours.

Example 2b

Matrix Formulations

| | Strength | | | | | | | | | | | |
|---|---|---|---|---|---|---|---|---|---|---|---|---|
| | 25 mg | | | 50 mg | | | 100 mg | | | 200 mg | | |
| Excipient | Slow | Medium | Fast | Slow | Medium | Fast | Slow | Medium | Fast | Slow | Medium | Fast |
| Lamotrigine | 25 mg (8.33%) | 25 mg (8.33%) | 25 mg (8.33%) | 50 mg (16.7%) | 50 mg (16.7%) | 50 mg (16.7%) | 100 mg (33.3%) | 100 mg (33.3%) | 100 mg (33.3%) | 200 mg (50%) | 200 mg (50%) | 200 mg (50%) |
| E4M | 52 | 32% | 17.5% | 26% | 23% | 20.5% | 22% | 19 | 16% | 15% | 8.7% | 5% |
| K100LV | 13 | 23% | 12.5% | 19% | 17% | 14.5% | 16% | 14 | 12% | 10% | 11.3% | 15% |
| Lactose* | qs | qs | q.s. | qs | q.s | q.s. | qs | q.s | qs | qs | qs | qs |
| Mg Stearate | 0.4% | 0.4% | 0.4% | 0.4% | | 0.4% | 0.4% | 0.4% | 0.4% | 0.4% | 0.4% | 0.4% |
| Tablet Weight (mg) | 300 | 300 | 300 | 300 | 300 | 300 | 300 | 300 | 300 | 400 | 400 | 400 |

In the above table slow represents tablets where 90% of the lamotrigine dissolved in vitro in 16 hours, medium where 90% of the lamotrigine is dissolved in 12 hours fast represents 90% of the lamotrigine dissolved in 6 hours.

The formulations described in Example 2 were prepared as set out in the flow diagram below.

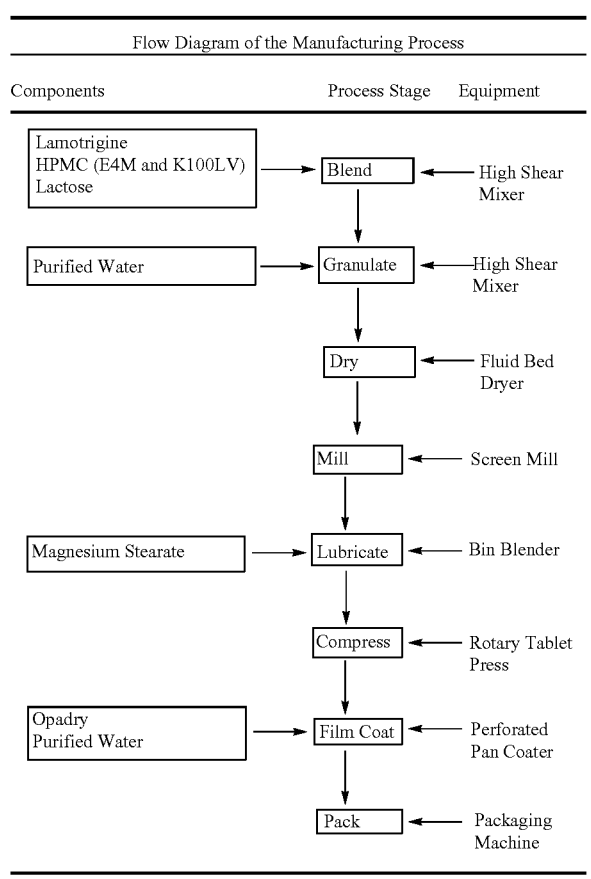

Example 3

Film Coated Formulations

| Component | Quantity (mg/tablet) | Quantity (% w/w) |
|---|---|---|
| Lamotrigine | 150 | 30.0 |
| Microcrystalline cellulose | 345 | 69.0 |
| Magnesium Stearate | 5 | 1.0 |
| Total Tablet Weight | 500 | 100 |

Bulk Preparation Method

First the components are weighed from bulk containers in the following amounts:

| Ingredients | Amount (KG) |
|---|---|
| Lamotrigine | 4.5 |
| Microcrystalline cellulose | 10.35 |
| Magnesium Stearate | 0.15 |

The components are then sieved using a Russel-SIV equipped with a 12 mesh (850 μm) or an equivalent sieve and mesh, and deposited into a stainless-steel blending container.

The lamotrigine and microcrystalline cellulose are blended for 15 minutes using a suitable blender, such as a Matcon-Buls bin-type blender, a V-blender or equivalent. The magnesium stearate is then added to the mixture and blending is continued for approximately 2 minutes.

The lubricated blend is then compressed using a suitable rotary tablet press, typically a Fette 2090 or equivalent. In-process controls for tablet weight and hardness are applied at appropriate intervals throughout the compression run and adjustments to the tablet press are made as necessary.

The tablets are then film-coated using O'Hara LabCoat II, or equivalent coater. Tablets are sprayed with a solution of Surelease and Opadry at either a 50/50 (solution A) or an 80/20 ratio (solution B). The aqueous coating solutions, A and B, are described below. Tablets were coated up to a 5% theoretical weight gain.

Coating Solution A

Weight out 162.5 grams of Surelease (E7-19060) and 162.5 g of Opadry (YS-2-7013) and placed into a suitable stainless steel mixing tank. Add 2437.5 grams of water. Mix until uniformed. Stir continually during application.

Coating Solution B

Weight out 260.00 grams of Surelease (E7-19060) and 65.00 g of Opadry (YS-2-7013) and placed into a suitable stainless steel mixing tank. Add 1061.67 grams of water. Mix until uniformed. Stir continually during application.

Example 4

DiffCORE Tablets

Formulation Details for DiffCORE Tablets, 25 mg

| Ingredients | Quantity (mg/tablet)[1] | |
|---|---|---|
| | Fast | Slow |
| CORE | | |
| Lamotrigine | 25 | 25 |
| Hydroxypropyl Methylcellulose (HPMC), K100LV, Prem CR USP/EP | 37.8 | 53.55 |
| Hydroxypropyl Methylcellulose (HPMC), E4M, Prem CR, USP | 52.2 | 73.95 |
| Lactose monohydrate, 200 mesh NF | 183.8 | 146.31 |
| Purified Water, EP/USP | | |
| Magnesium Stearate, EP/NF | 1.2 | 1.2 |
| OUTER COAT | | |
| Eudragit L30 D-55 (30% w/w solution) | 13.08 | 12.98 |
| Red Iron Oxide, USP | 0.15 | 0.278 |
| Triethyl Citrate, NF | 1.37 | 1.36 |
| Glyceryl Monostearate, NF | 0.37 | 0.37 |
| Polysorbate 80, NF | 0.016 | 0.016 |
| Purified Water EP/USP | | |

[1] Fast represents a release period of 12 hours and slow represents a release period of 15 hours.

Formulation Example of DiffCORE Tablets, 200 mg

| Ingredients | Quantity (mg/tablet)[1] Slow |
|---|---|
| CORE | |
| Lamotrigine | 200 |
| Hydroxypropyl Methylcellulose (HPMC), K100LV, Prem CR USP/EP | 62.64 |
| Hydroxypropyl Methylcellulose (HPMC), E4M, Prem CR, USP | 45.36 |
| Lactose monohydrate, 200 mesh NF | 90.4 |
| Purified Water, EP/USP | |
| Magnesium Stearate, EP/NF | 1.6 |
| OUTER COAT | |
| Eudragit L30 D-55 (30% w/w solution) | 17.3 |
| Red Iron Oxide, USP | 0.37 |
| Triethyl Citrate, NF | 1.81 |
| Glyceryl Monostearate, NF | 0.494 |
| Polysorbate 80, NF | 0.02 |
| Purified Water EP/USP | |

The core of the tablets were prepared as described in Example 2 and subsequently coated.

Coating

The tablets were film-coated using a standard coating machine e.g. a Vector™ machine purchased from Vector, or equivalent coater. Tablets were sprayed with an aqueous solution of Eudragit 10% w/w as described below. Tablets were coated up to a 5% theoretical weight gain.

Example of 10% Coating Solution Preparation

Part A 350 ml Eudragit L30 D55 30% solution was diluted with 150 ml of water. 11 g of Triethyl Citrate was added and the solution mixed thoroughly.

Part B 440 g of purified water was added to a separate vessel and heated to approximately 60 C. Using appropriate mixer (high shear) for Kalish mixture 0.13 g of Polysorbate 80 NF and 3.0 g of Glyceryl Monostearate, NF were incorporated into solution. 4.0 g of iron oxide was added and homogenised for 15 minute at high speed.

Part A and Part B were combined and the final weight adjusted with purified water to 1000 g and mixed.

Drilling

The tablets were drilled mechanically using a standard drill press. A tablet was placed in a tablet holder and carefully drilled until the film coat was removed from the drilled surface, then the tablet was flipped over and the opposite side subsequently drilled. Upon completion the drilled tablet was inspected for weight loss (orifice depth), quality of the orifice edge and overall appearance.

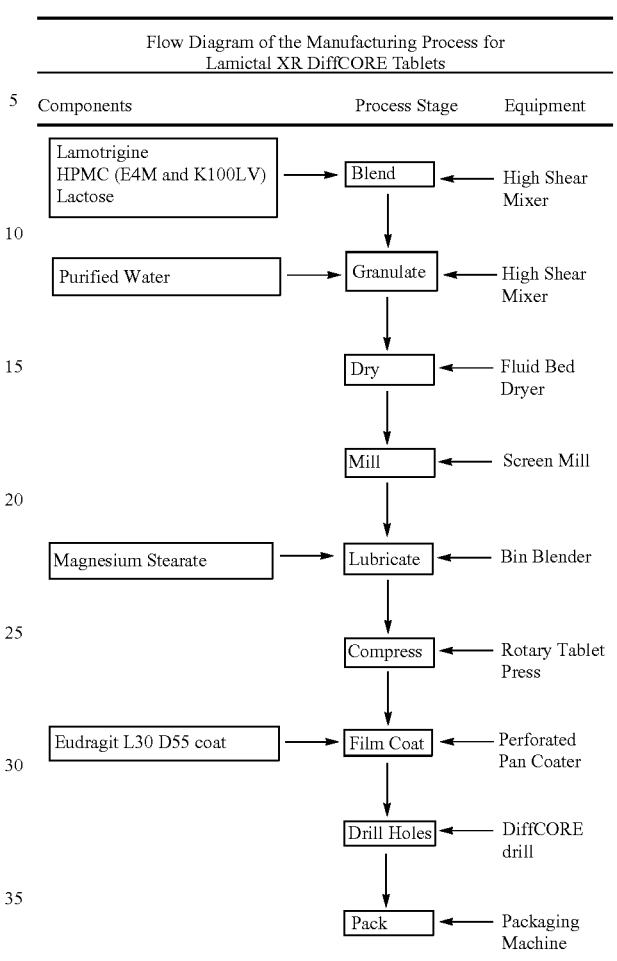

Flow Diagram of the Manufacturing Process for Lamictal XR DiffCORE Tablets

Example 5

Pharmacokinetic Study to Investigate Lamotrigine Sustained Release Formulation in Humans The in vivo disposition of the lamotrigine sustained release formulation was initially assessed in a healthy volunteer pharmacokinetic study. The study was of an incomplete block design consisting of 2 doses (e.g., 25 mg (granule strength 1) and 200 mg (granule strength 2)) and 3 different sustained release rates at each dose, with the IR formulation as a reference. Each volunteer participated in 4 out of the possible 7 arms/formulations. For each formulation, blood samples were collected from each volunteer over a specified period of time for the measurement of lamotrigine serum concentrations and, consequently, the derivation of lamotrigine pharmacokinetic parameters. Safety and tolerability of each formulation was also be assessed.

Example 6

Pharmacokinetic Study to Investigate Lamotrigine Sustained Release Formulation in Humans Formulations as described in Example 2 were investigated in a human volunteer study as described in Example 5. The 25 mg and 200 mg slow, medium and fast formulations were dosed to human volunteers and mean 0-36 hour PK profiles were obtained and are shown in FIG. 5.

The different release rates of the tablets described in Example 2 resulted in different PK profiles: the AUC values for different rates were comparable to IR tablets, with the $C_{max}$ being reduced by up to approximately 30%.

Example 7

Pharmacokinetic Study to Investigate Lamotrigine Sustained Release Formulation in Humans Formulations as described in Example 4 were investigated in a human volunteer study comprising 29 volunteers. All volunteers received a single dose of the IR tablet (Regime A) and 25 mg DiffCore Slow tablet (Regime C) and one of either 25 mg DiffCore Fast tablet (Regime B), 25 mg DiffCore Slow tablet with a high fat breakfast (Regime D) or the 200 mg Diffcore Slow tablet (Regime E). The formulations were dosed to human volunteers and mean serum concentrations-time profiles from 0 to 144 hours and are shown for Regimes A, B, C and D in FIG. 8. The $AUC_{(0-\infty)}$ values of the 25 mg tablets were comparable to the 25 mg IR tablets and the Cmax being reduced by up to approximately 30%. The 200 mg IR profile from the study outlined in Example 6 and the profile of the 200 mg DiffCORE tablet from Example 4 from study outlined in Example 7 are shown in FIG. 9.

A further aspect of the invention is a pharmaceutical formulation as described in any one of Examples 1 to 4.

| Tradename | Generic description | Supplier |
|---|---|---|
| Methocel E4M | hydroxypropyl methylcellulose with 28-30% methoxyl and 8.5% hydroxypropyl substitution, having a 4,000 mPa s nominal viscosity (2% solution in water) | Dow |
| Methocel K15M | hydroxypropyl methylcellulose with 22% methoxyl and 8.1% hydroxypropyl substitution, having a 15,000 mPa s nominal viscosity (2% solution in water) | Dow |
| Methocel K100M | hydroxypropyl methylcellulose with 22% methoxyl and 8.1% hydroxypropyl substitution, having a 100,000 mPa s nominal viscosity (2% solution in water) | Dow |
| Methocel K4M | hydroxypropyl methylcellulose with 22% methoxyl and 8.1% hydroxypropyl substitution, having a 4,000 mPa s nominal viscosity (2% solution in water) | Dow |
| Methocel E5 | hydroxypropyl methylcellulose with 29% methoxyl and 8.5% hydroxypropyl substitution, having a 5 mPa s nominal viscosity (2% solution in water) | Dow |
| Methocel E5M | hydroxypropyl methylcellulose with 29% methoxyl and 8.5% hydroxypropyl substitution, having a 5,000 mPa s | Dow |
| Methocel E50 | hydroxypropyl methylcellulose with 29% methoxyl and 8.5% hydroxypropyl substitution, having a 50 mPa s nominal viscosity (2% solution in water) | Dow |
| Methocel K100LV | low viscosity Hydroxypropyl Methylcellulose | Dow |
| POLYOX ™ WSRN-80 | high molecular weight water-soluble poly (ethylene oxide) polymer. Molecular weight of 200,000, having a nominal viscosity of 55-90 cP (5% solution). | Dow |
| Opadry (YS-2-7013) | hydroxypropylmethylcellulose aqueous dispersion | Colorcon |
| Surelease (E-7-19010) | aqueous ethylcellulose dispersion | Colorcon |
| Eudragit ® L30D-55 | methacrylic acid - ethyl acrylate copolymer | Rohm Pharma |
| Eudragit ® RS 30D | ammonium-methacrylic copolymer RL = 10% quat. ammonium RS = 5% quat. ammonium | Rohm Pharma |
| Eudragit ® RL 30D | | |
| Aquacoat | ethylcellulose latex suspension | (FMC) |

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

What is claimed is:

1. A sustained release formulation of lamotrigine, which has a mean serum lamotrigine concentration-time profile as shown in or substantially similar to that shown in the second graph of FIG. 8, comprising a matrix tablet in which there are two phases in the release of lamotrigine, wherein the release rate in the first phase takes place in the oesophagus and stomach and said release is slower than the release rate in the second phase which takes place when the surrounding pH exceeds 5, wherein the sustained release formulation comprises:
   1) a core comprising:
      a) 2.5 to 80% by weight lamotrigine;
      b) 17.5 to 70% by weight release retarding hydroxypropylmethylcellulose polymer which comprises Methocel E4M and Methocel K100LV;
      c) 0 to 60% by weight diluent;
      d) 0 to 20% by weight compression aid;
      e) 0.1 to 2.5% by weight lubricants; and
   2) an outer coat covering said core comprising:
      f) 0.05 mm to 0.30 mm of methacrylic copolymer which is Eudragit L30 D55;
   in which the thickness of said outer coating is adapted such that it is substantially impermeable to the entrance of an environmental fluid, substantially impermeable to the exit of lamotrigine, dissolves when the surrounding pH exceeds 5; and
   includes one or more orifices extending from the outside of the coating substantially completely through said coating but not penetrating said core allowing the release of lamotrigine from the core into environmental fluid, said orifices having an area or combined area from about 10 to about 60 percent of the face area of said formulation, wherein the release of lamotrigine occurs substantially through said orifice.

2. A sustained release formulation as claimed in claim 1 which upon administration to a human produces AUC values within the range of 80 to 125% and a $C_{max}$ being of about 30% less than an instant release tablet containing the same amount of lamotrigine.

3. A sustained release formulation of lamotrigine, which has a mean serum lamotrigine concentration-time profile as shown in or substantially similar to that shown in the second graph of FIG. 8, comprising a matrix tablet in which there are two phases in the release of lamotrigine, wherein the release rate in the first phase takes place in the oesophagus and stomach and said release is slower than the release rate in the second phase which takes place when the surrounding pH exceeds 5, wherein the formulation comprises:
1) a core comprising:
   a) 2.5 to 80% by weight lamotrigine;
   b) 17.5 to 70% by weight release retarding hydroxypropylmethylcellulose polymer which comprises Methocel E4M and Methocel K100LV;
   c) 0 to 60% by weight diluent;
   d) 0 to 20% by weight compression aid;
   e) 0.1 to 2.5% by weight lubricants; and
2) an outer coat covering said core comprising:
   f) 0.05 mm to 0.30 mm of methacrylic copolymer which is Eudragit L30 D55;
in which the thickness of said outer coating is adapted such that it is substantially impermeable to the entrance of an environmental fluid, substantially impermeable to the exit of lamotrigine, dissolves when the surrounding pH exceeds 5; and
includes one or more orifices extending from the outside of the coating substantially completely through said coating but not penetrating said core, allowing the release of lamotrigine from the core into environmental fluid, said orifices having an area or combined area from about 10 to about 60 percent of the face area of said formulation, wherein the release of lamotrigine occurs substantially through said orifice, and said sustained release formulation upon administration to a human produces AUC values within the range of 80 to 125% and a $C_{max}$ being of about 30% less than an instant release tablet containing the same amount of lamotrigine.

* * * * *

UNITED STATES PATENT AND TRADEMARK OFFICE
CERTIFICATE OF CORRECTION

PATENT NO. : 8,637,512 B2
APPLICATION NO. : 10/726752
DATED : January 28, 2014
INVENTOR(S) : Buxton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1989 days.

Signed and Sealed this
Fifth Day of May, 2015

Michelle K. Lee
*Director of the United States Patent and Trademark Office*